(12) United States Patent
Ren et al.

(10) Patent No.: US 7,736,756 B2
(45) Date of Patent: Jun. 15, 2010

(54) LIGHT EMITTING DEVICE CONTAINING PHOSPHORESCENT COMPLEX

(75) Inventors: Xiaofan Ren, Rochester, NY (US); Shouquan Huo, Webster, NY (US)

(73) Assignee: Global OLED Technology LLC, Wilmington, DE (US)

( * ) Notice: Subject to any disclaimer, the term of this patent is extended or adjusted under 35 U.S.C. 154(b) by 719 days.

(21) Appl. No.: 11/680,663

(22) Filed: Mar. 1, 2007

(65) Prior Publication Data

US 2008/0020237 A1 Jan. 24, 2008

Related U.S. Application Data

(63) Continuation-in-part of application No. 11/488,435, filed on Jul. 18, 2006.

(51) Int. Cl.
*H01L 51/54* (2006.01)
*C09K 11/06* (2006.01)

(52) U.S. Cl. .................. 428/690; 428/917; 313/504; 313/506; 252/301.16; 257/40; 257/102; 257/E51.044; 546/4; 546/10

(58) Field of Classification Search ............... None
See application file for complete search history.

(56) References Cited

U.S. PATENT DOCUMENTS

2002/0034656 A1    3/2002   Thompson et al.

| | | | |
|---|---|---|---|
| 2002/0086180 A1 * | 7/2002 | Seo et al. ............... | 428/690 |
| 2003/0017361 A1 | 1/2003 | Thompson et al. | |
| 2003/0235712 A1 * | 12/2003 | Takiguchi et al. ......... | 428/690 |
| 2004/0053071 A1 * | 3/2004 | Igarashi et al. .......... | 428/690 |
| 2005/0275341 A1 * | 12/2005 | Satsuki et al. ........... | 313/504 |

FOREIGN PATENT DOCUMENTS

WO    01/41512    6/2001

OTHER PUBLICATIONS

Zhang et al. "Free radical reactions for heterocycle synthesis. Part 6: 2-Bromobenzoic acids as building blocks in the construction of nitrogen heterocycles." Tetrahedron 2003. vol. 59, pp. 3009-3018.*
S. Lamansky, et al., "Highly Phosphorescent Bis-Cyclometalated Iridium Complexes: Synthesis, Photophysical Characterization, and Use in Organic Light Emitting Diodes", J.; Am. Chem. Soc., 2001, 123, pp. 4304-4312.

* cited by examiner

*Primary Examiner*—D. Lawrence Tarazano
*Assistant Examiner*—Michael Wilson
(74) *Attorney, Agent, or Firm*—McKenna Long & Aldridge LLP

(57) ABSTRACT

An OLED device comprises a cathode, an anode, and has therebetween a light emitting layer comprising a phosphorescent emitter represented by Formula (I):

$$L_nM \qquad (I)$$

wherein each L is a cyclometallated ligand with at least one containing a coumarin group, M is Ir or Pt, and n is 3 when M is Ir and 2 when M is Pt. The invention also comprised the compound of formula (I).

5 Claims, 1 Drawing Sheet

LIGHT EMITTING DEVICE CONTAINING PHOSPHORESCENT COMPLEX

CROSS-REFERENCE TO RELATED APPLICATIONS

This application is a Continuation-in-Part of U.S. Ser. No. 11/488,435 filed on Jul. 18, 2006, the contents of which are incorporated herein by reference.

FIELD OF INVENTION

This invention relates to organic electroluminescent (EL) devices and compounds contained therein. More specifically, this invention relates to very efficient devices containing certain phosphorescent organometallic complexes.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322-334, 1969; and Dresner U.S. Pat. No. 3,710,167, issued Jan. 9, 1973. The organic layers in these devices, usually composed of a polycyclic aromatic hydrocarbon, were very thick (much greater than 1 μm). Consequently, operating voltages were very high, often >100V.

More recent organic EL devices include an organic EL element consisting of extremely thin layers (e.g. <1.0 μm) between the anode and the cathode. Herein, the term "organic EL element" encompasses the layers between the anode and cathode electrodes. Reducing the thickness lowered the resistance of the organic layer and has enabled devices that operate at a much lower voltage. In a basic two-layer EL device structure, described first in U.S. Pat. No. 4,356,429, one organic layer of the EL element adjacent to the anode is specifically chosen to transport holes, therefore, it is referred to as the hole-transporting layer, and the other organic layer is specifically chosen to transport electrons, referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by Tang et al [*J. Applied Physics*, Vol. 65, Pages 3610-3616, 1989]. The light-emitting layer commonly consists of a host material doped with a guest material. Still further, there has been proposed in U.S. Pat. No. 4,769,292 a four-layer EL element comprising a hole-injecting layer (HIL), a hole-transporting layer (HTL), a light-emitting layer (LEL) and an electron transporting/injecting layer (ETL). These structures have resulted in improved device efficiency.

Many emitting materials that have been described as useful in an OLED device emit light from their excited singlet state by fluorescence. The excited singlet state is created when excitons formed in an OLED device transfer their energy to the excited state of the dopant. However, it is generally believed that only 25% of the excitons created in an EL device are singlet excitons. The remaining excitons are triplet, which cannot readily transfer their energy to the singlet excited state of a dopant. This results in a large loss in efficiency since 75% of the excitons are not used in the light emission process.

Triplet excitons can transfer their energy to a dopant if it has a triplet excited state that is low enough in energy. If the triplet state of the dopant is emissive it can produce light by phosphorescence. In many cases singlet excitons can also transfer their energy to lowest singlet excited state of the same dopant. The singlet excited state can often relax, by an inter-system crossing process, to the emissive triplet excited state. Thus, it is possible, by the proper choice of host and dopant, to collect energy from both the singlet triplet excitons created in an OLED device and to produce a very efficient phosphorescent emission.

Typical phosphorescent dopants are organometallic compounds, in particular iridium is often used as the metal. A common green phosphorescent dopant is fac-tris(phenylpyridine) (Ir(ppy)$_3$) see *Appl. Phys. Lett.* 1999, 75, 4. By changing the ligands attached to the metal the properties of the materials when used in an OLED device may be modified. A different iridium organometallic compound such as fac-tris (2-(4',5'-difluorophenyl)pyridine-C,N)iridium(III) (*Polymer preprints* 2000, 41(1), 770) emits blue light. Emission color is not the only important property of phosphorescent dopants. The usefulness of a dopant for an OLED device is dependent on the device's drive voltage, luminance, efficiency, and lifetime.

Notwithstanding these developments, there remains a need for new organometallic compounds that will function as phosphorescent dopants having improved device drive voltage, luminance, efficiency, and lifetime.

SUMMARY OF THE INVENTION

The invention provides an OLED device comprising a cathode, an anode, and having therebetween a light emitting layer comprising a phosphorescent emitter represented by Formula (I):

$$L_nM \qquad (I)$$

wherein each L is a cyclometallated ligand with at least one containing a coumarin group, M is Ir or Pt, and n is 3 when M is Ir and 2 when M is Pt.

The devices of the invention exhibit improved device drive voltage, luminance, efficiency, and lifetime.

The invention also provides a compound represented by Formula (I):

$$L_nM \qquad (I)$$

wherein each L is a cyclometallated ligand with at least one containing a coumarin group, M is Ir or Pt, and n is 3 when M is Ir and 2 when M is Pt.

DETAILED DESCRIPTION OF THE INVENTION

Figure 1:
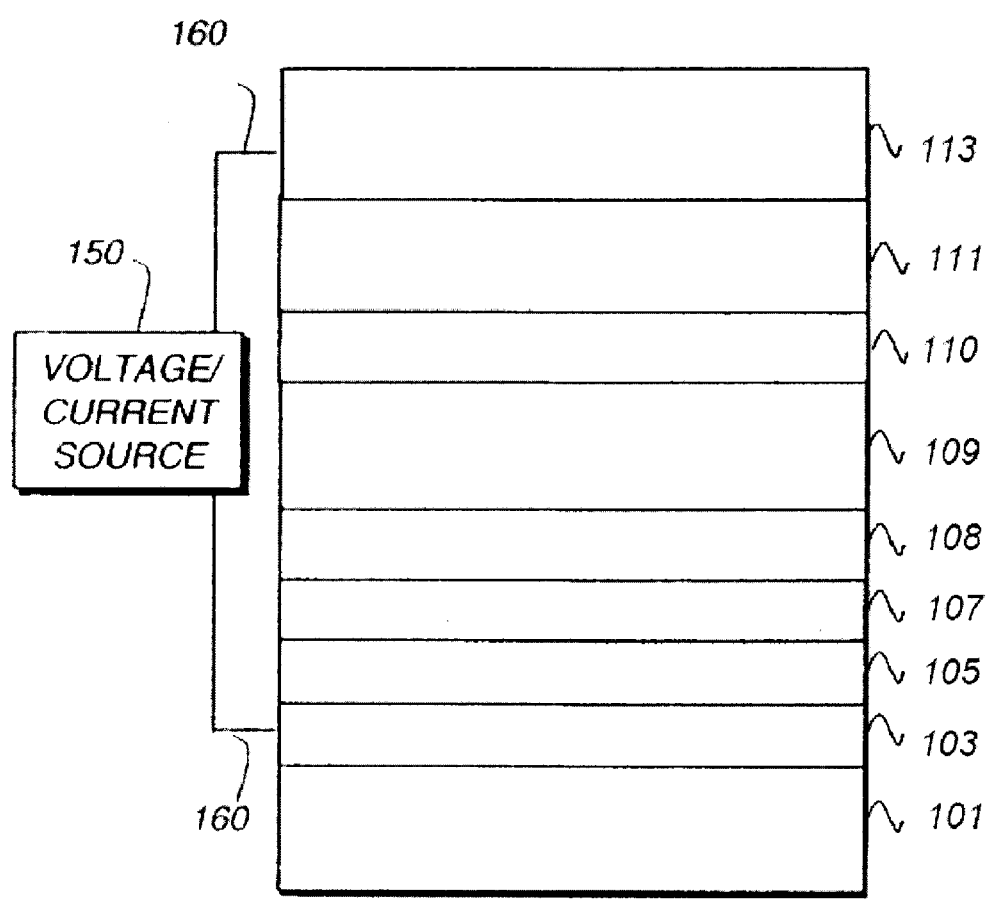
FIG. 1 shows a schematic cross-section of a typical OLED device in which this invention may be used.

The invention provides an OLED device comprising a cathode, an anode, and having therebetween a light emitting layer comprising a phosphorescent emitter represented by Formula (I):

$$L_nM \qquad (I)$$

wherein each L is a cyclometallated ligand with at least one containing a coumarin group, M is Ir or Pt, and n is 3 when M is Ir and 2 when M is Pt.

A cyclometallated ligand is one that is attached to the metal atom through a carbon metal bond. These are typically formed through C—H oxidative additions as explained in *Principles and Applications of Organotransition Metal Chemistry* page 298, by Collman, Hegedus, Norton, and Finke. It is possible that the carbon metal bond may be formed through other means besides C—H oxidative addition. An example of this term in use is shown in *J. Am. Chem. Soc.* 2001, 123, 4304-431.

In one embodiment, the phosphorescent emitter represented by Formula (I) may be a homoleptic facial isomer. In another embodiment the phosphorescent emitter represented by Formula (I) may be a heteroleptic facial isomer.

In one embodiment at least one L group of Formula (I) is 2-phenyl-pyridinato-N,C$^{2'}$ (ppy).

In a preferred embodiment the phosphorescent emitter is represented by Formula (II):

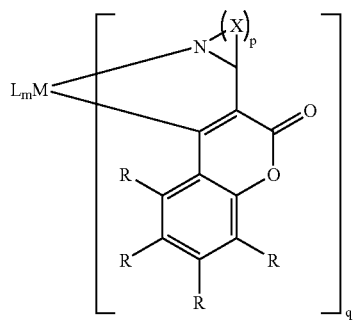

(II)

where M is Ir or Pt; each L independently represents a cyclometallated ligand; each X independently represents the atoms necessary to form a ring; each R independently represents hydrogen or a substituent, provided that two adjacent R groups are able to form a ring; each p independently represents an integer from 3 to 6; m is a integer from 0 to 2; and q is a integer from 1 to 3.

In one embodiment, M of Formula (II) is iridium.

In a further preferred embodiment, the phosphorescent emitter is represented by Formula (III):

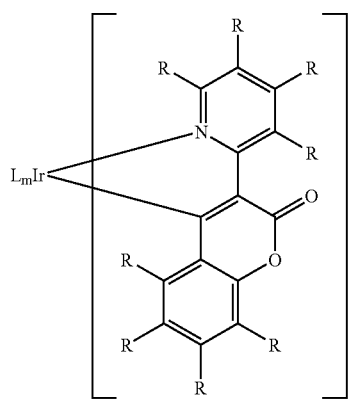

(III)

wherein each L independently represents a cyclometallated ligand; each R independently represents hydrogen or a substituent, provided that two adjacent R groups are able to form a ring; m is a integer from 0 to 2; q is a integer from 1 to 3; and the sum of m+q is 3.

In a further preferred embodiment, the phosphorescent emitter is represented by Formula (IV):

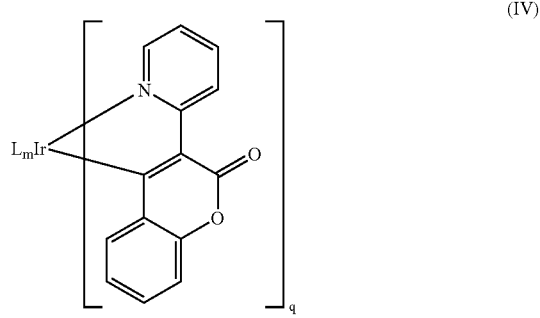

(IV)

where each L independently represents a cyclometallated ligand; m is a integer from 0 to 2; q is a integer from 1 to 3; and the sum of m+q is 3.

In another preferred embodiment the phosphorescent emitter is represented by Formula (V):

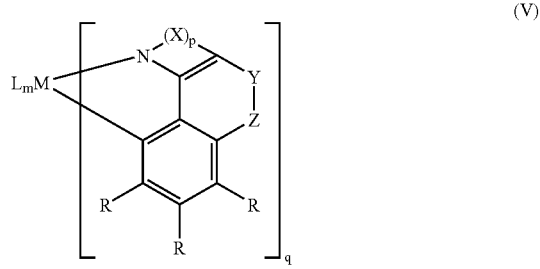

(V)

where M is Ir or Pt; each L independently represents a cyclometallated ligand; each X independently represents the atoms necessary to form a substituted or unsubstituted ring; each R independently represents hydrogen or a substituent, provided that two adjacent R groups are able to form a ring; Y and Z are each independently an oxygen atom and a carbonyl group such that when one is a carbonyl group the other is an oxygen atom; p is an integer from 2 to 4; m is a integer from 0 to 2; and q is a integer from 1 to 3.

In one embodiment, M of Formula (V) is iridium.

In a further preferred embodiment, the phosphorescent emitter is represented by Formula (VI):

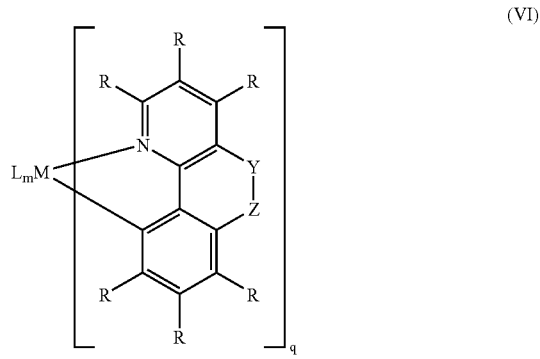

(VI)

where each L independently represents a cyclometallated ligand; each R independently represents hydrogen or a substituent, provided that two adjacent R groups are able to form a ring; Y and Z are each independently an oxygen atom and a carbonyl group such that when one is a carbonyl group the other is an oxygen atom; m is an integer from 0 to 2; q is a integer from 1 to 3; and the sum of m+q is 3.

In a further preferred embodiment, the phosphorescent emitter is represented by Formula (VII):

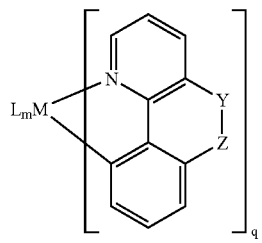

(VII)

where each L independently represents a cyclometallated ligand; Y and Z are each independently an oxygen atom and a carbonyl group such that when one is a carbonyl group the other is an oxygen atom; m is a integer from 0 to 2; q is a integer from 1 to 3; and the sum of m+q is 3.

In one embodiment, the phosphorescent emitter comprises 0.5% to 15% of the light emitting layer. In a preferred embodiment the phosphorescent emitter comprises 1% to 10% of the light emitting layer, or may comprises 6% to 9% of the light emitting layer.

An OLED device may comprise at least one additional emitter to enable the device to emit white light. The second or additional colors are typically complementary colors. For example, if one compound is a blue emitter a second compound would emit yellow in order for the device to emit white light. Three emitter which each emit different colored light such as red, green, and blue; would be useful.

A useful embodiment comprises a light emitting layer containing an electron transporting host and a hole transporting host. Examples of classes of compounds useful in the light emitting layer are: carbazoles, aryl amines, benzazoles, phenanthrolines and compounds represented by Figure PHF-7

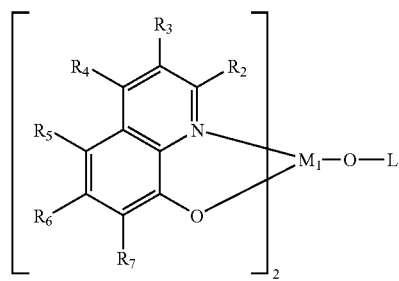

(PHF-7)

where $M_1$ represents Al or Ga; each $R_2$-$R_7$ independently represent hydrogen or a substituent; provided adjacent substituents, $R_2$-$R_7$, may combine to form a ring group; and L is an aromatic substituent which has from 6 to 30 carbon atoms.

Specific examples of compounds useful in the light emitting layer are:
9,9'-[1,1'-biphenyl]-4,4'-diylbis-9H-carbazole (CBP);
2,2',2"-(1,3,5-phenylene)tris(1-phenyl-1H-benzimidazole) (TPBI) and
4,4',4"-tris(carbazolyl)-triphenylamine (TCTA);
4,4',4"-tris[(3-methylphenyl)phenylamino]triphenylamine (MTDATA);
4,4',4"-tris(N,N-diphenylamino)triphenylamine (TDATA);
tetraphenyl-p-phenylenediamine (TPPD);

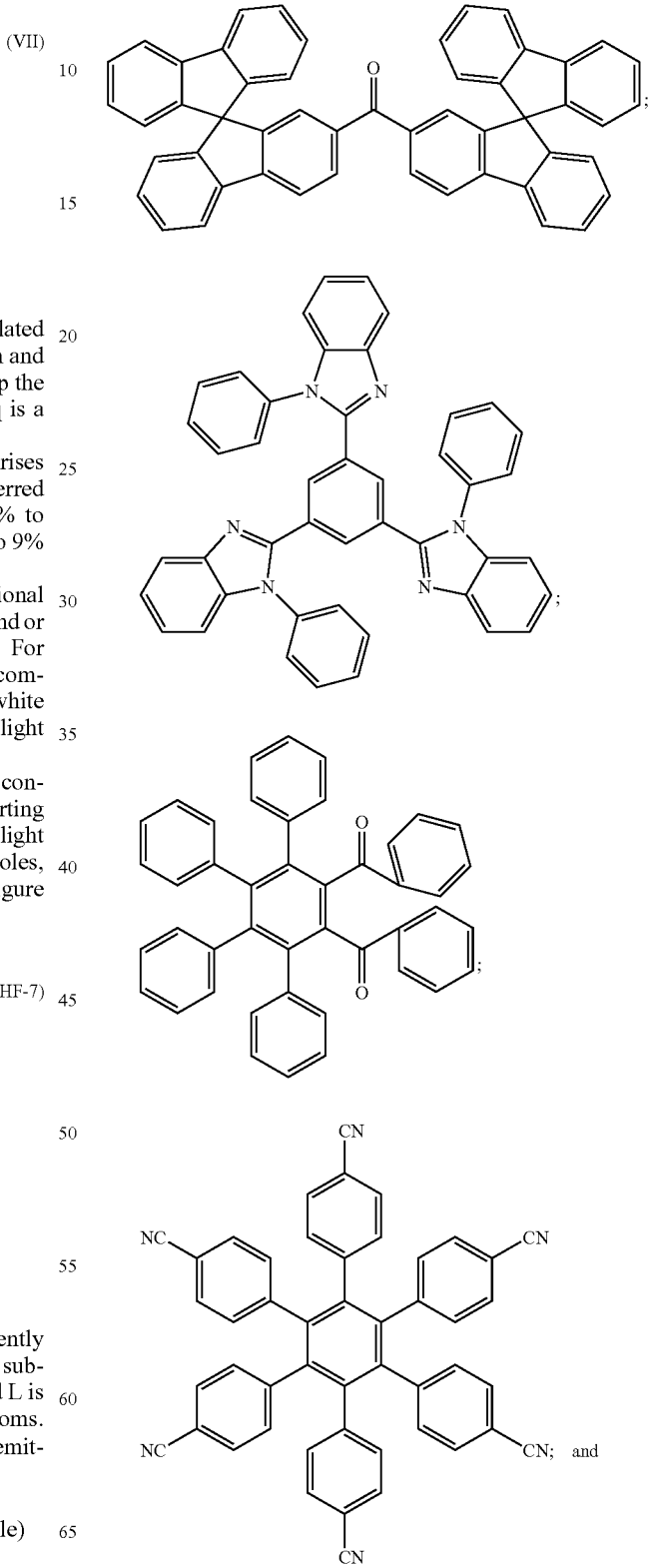

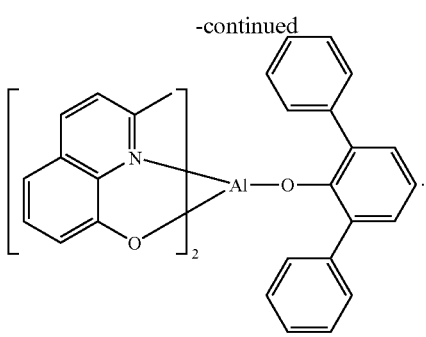

In one embodiment, the compound represented by Formula (I):

$$L_nM \tag{I}$$

wherein each L is a cyclometallated ligand with at least one containing a coumarin group, M is Ir or Pt, and n is 3 when M is Ir and 2 when M is Pt.

Embodiments of the invention can provide advantageous features such as operating efficiency, higher luminance, color hue, low drive voltage, and improved operating stability. Embodiments of the organometallic compounds useful in the invention can provide a wide range of hues including those useful in the emission of white light (directly or through filters to provide multicolor displays).

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for device utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur or phosphorous, such as pyridyl, thienyl, furyl, azolyl, thiazolyl, oxazolyl, imidazolyl, pyrazolyl, pyrazinyl, pyrimidinyl, pyrolidinonyl, quinolinyl, isoquinolinyl, 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The definition of a heterocyclic ring are those rings that include coordinate or dative bonds. The definition of a coordinate bond can be found in *Grant & Hackh's Chemical Dictionary*, page 91. In essence, a coordinate bond is formed when electron rich atoms such as O or N, donate a pair of electrons to electron deficient atoms such as Al or B.

It is well within the skill of the art to determine whether a particular group is electron donating or electron accepting. The most common measure of electron donating and accepting properties is in terms of Hammett σ values. Hydrogen has a Hammett σ value of zero, while electron donating groups have negative Hammett σ values and electron accepting groups have positive Hammett σ values. Lange's handbook of Chemistry, 12$^{th}$ Ed., McGraw Hill, 1979, Table 3-12, pp. 3-134 to 3-138, here incorporated by reference, lists Hammett σ values for a large number of commonly encountered groups. Hammett σ values are assigned based on phenyl ring substitution, but they provide a practical guide for qualitatively selecting electron donating and accepting groups.

Suitable electron donating groups may be selected from —R', —OR', and —NR'(R") where R' is a hydrocarbon containing up to 6 carbon atoms and R" is hydrogen or R'. Specific examples of electron donating groups include methyl, ethyl, phenyl, methoxy, ethoxy, phenoxy, —N(CH$_3$)$_2$, —N(CH$_2$CH$_3$)$_2$, —NHCH$_3$, —N(C$_6$H$_5$)$_2$, —N(CH$_3$)(C$_6$H$_5$), and —NHC$_6$H$_5$.

Suitable electron accepting groups may be selected from the group consisting of cyano, α-haloalkyl, α-haloalkoxy, amido, sulfonyl, carbonyl, carbonyloxy and oxycarbonyl substituents containing up to 10 carbon atoms. Specific examples include —CN, —F, —CF$_3$, —OCF$_3$, —CONHC$_6$H$_5$, —SO$_2$C$_6$H$_5$, —COC$_6$H$_5$, —CO$_2$C$_6$H$_5$, and —OCOC$_6$H$_5$.

Unless otherwise specified, the term "percentage" or "percent" and the symbol "%" of a material indicates the volume percent of the material in the layer in which it is present.

Compounds useful for the invention include:

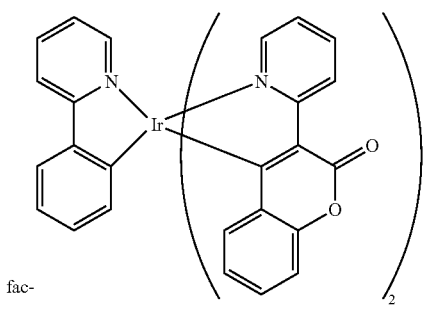

fac- INV-1

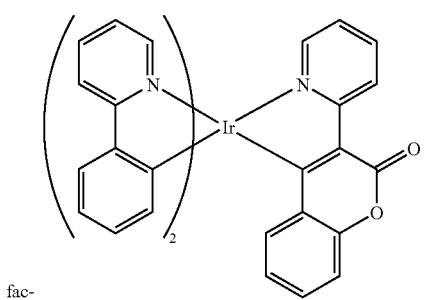

fac- INV-2

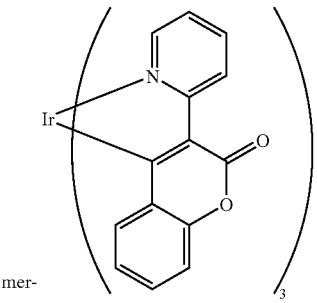

mer- INV-3

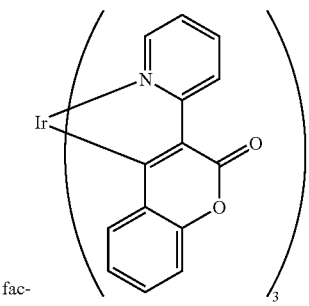

fac- INV-4

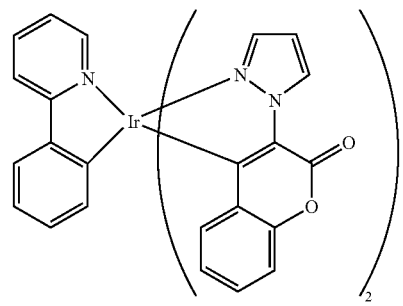

INV-5

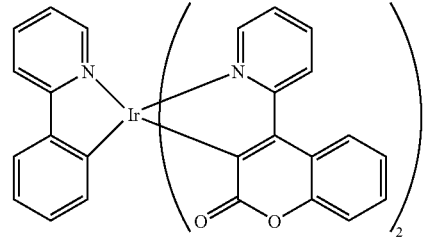

INV-6

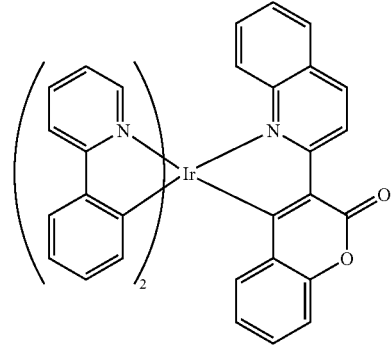

INV-7

-continued
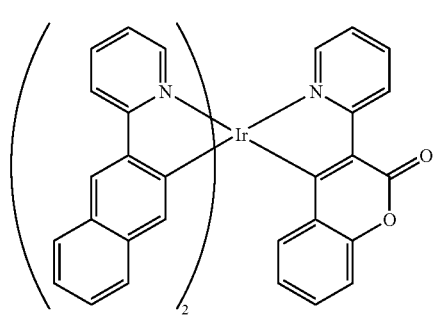
INV-8
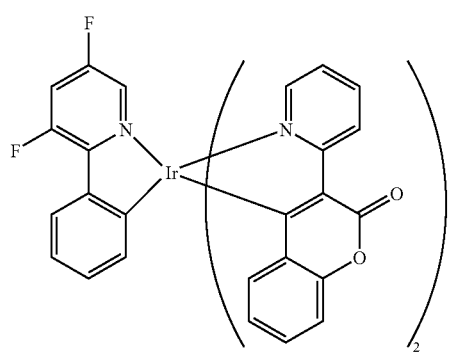
INV-9
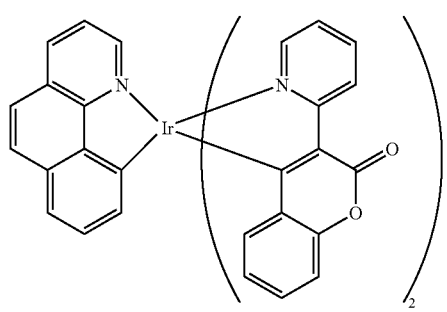
INV-10
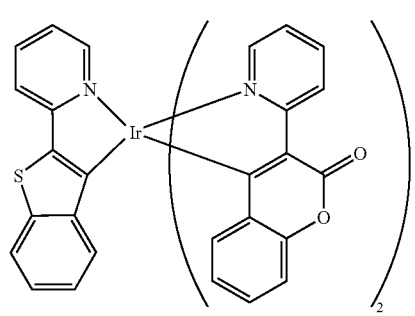
INV-11
-continued
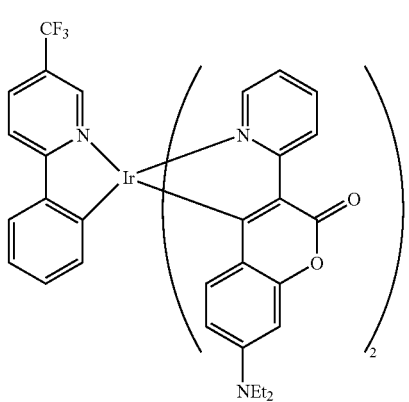
INV-12
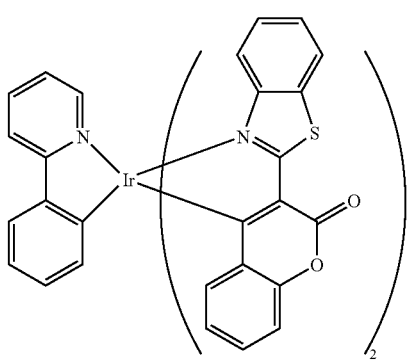
INV-13
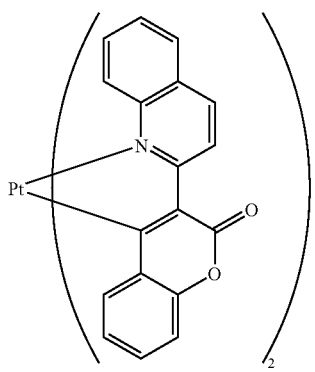
INV-14
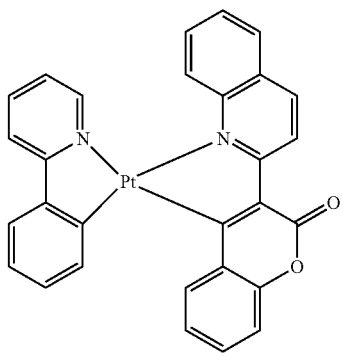
INV-15

-continued
INV-16
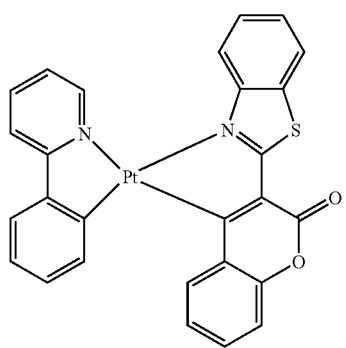
INV-17
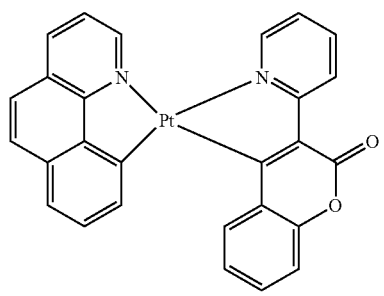
INV-18
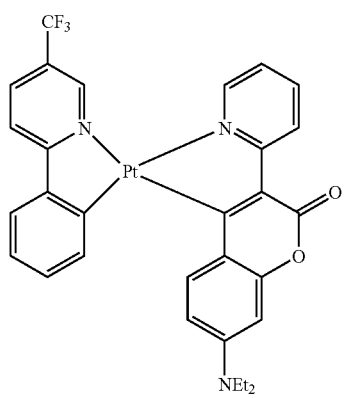
INV-19
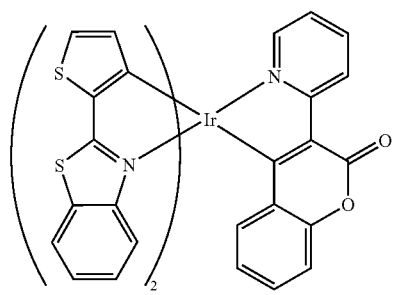
INV-20
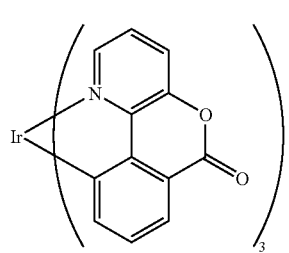
-continued
INV-21
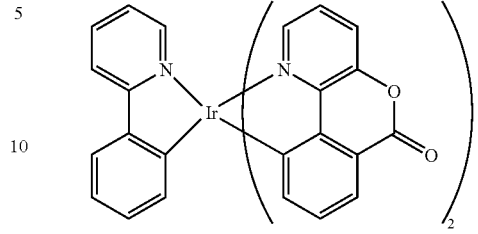
INV-22
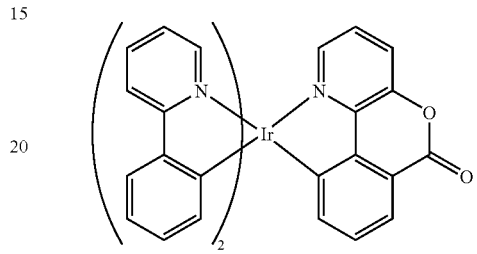
INV-23
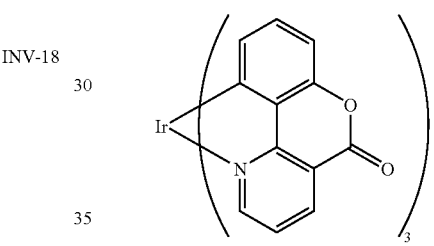
INV-24
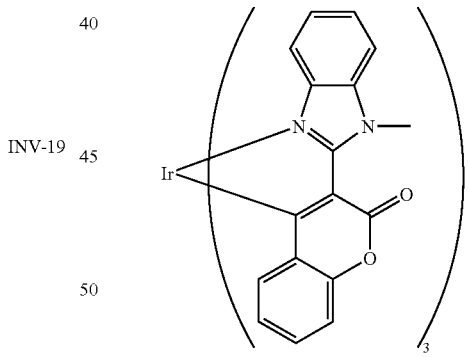
INV-25
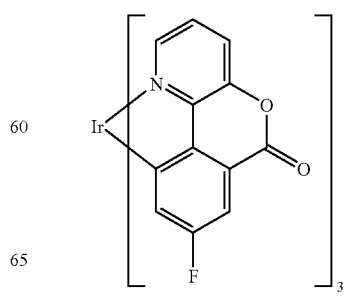

-continued

INV-26
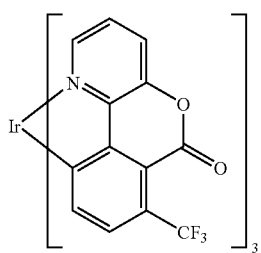

INV-27
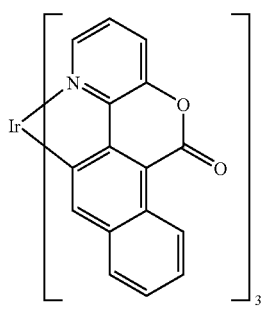

INV-28
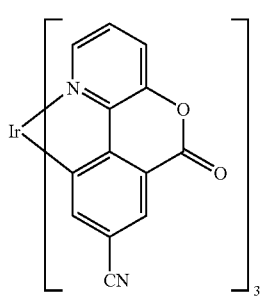

INV-29
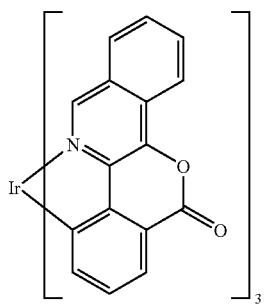

INV-30
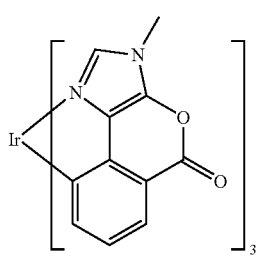

-continued

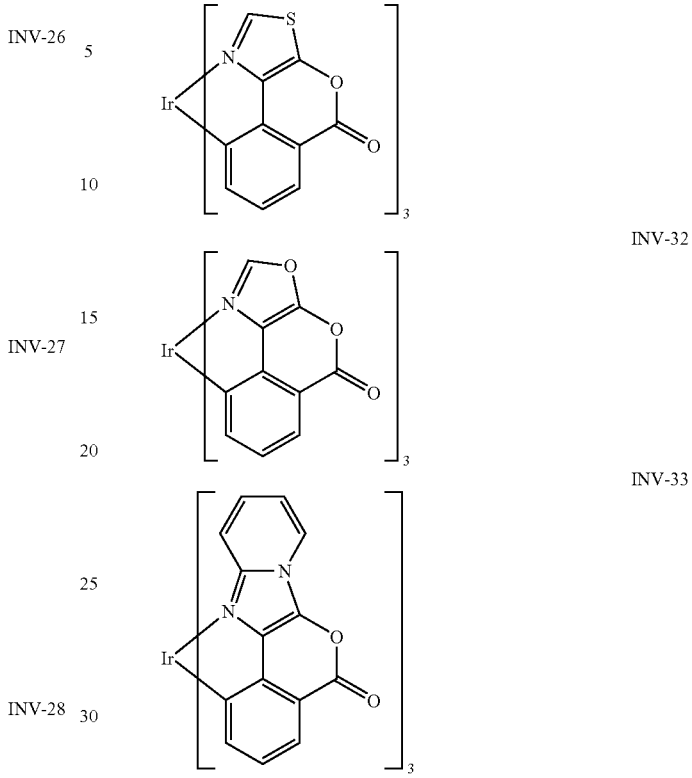

INV-31

INV-32

INV-33

Some embodiments of the invention may provide advantageous features such as operating efficiency, higher luminance, color hue, low drive voltage, and improved operating stability. Embodiments of the organometallic compounds useful in the invention may provide a wide range of hues including those useful in the emission of white light (directly or through filters to provide multicolor displays).

General Device Architecture

The present invention can be employed in many OLED device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers. The essential requirements of an OLED are an anode, a cathode, and an organic light-emitting layer located between the anode and cathode. Additional layers may be employed as more fully described hereafter.

A typical structure, especially useful for of a small molecule device, is shown in FIG. 1 and is comprised of a substrate 101, an anode 103, a hole-injecting layer 105, a hole-transporting layer 107, an exciton blocking layer 108, a light-emitting layer 109, a hole- or exciton-blocking layer 110, an electron-transporting layer 111, and a cathode 113. These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is desirably less than 500 nm.

The anode and cathode of the OLED are connected to a voltage/current source 150 through electrical conductors 160. The OLED is operated by applying a potential between the anode and cathode such that the anode is at a more positive potential than the cathode. Holes are injected into the organic EL element from the anode and electrons are injected into the organic EL element at the cathode. Enhanced device stability can sometimes be achieved when the OLED is operated in an AC mode where, for some time period in the cycle, the potential bias is reversed and no current flows. An example of an AC driven OLED is described in U.S. Pat. No. 5,552,678.

Substrate

An OLED device is typically provided over a supporting substrate 101 where either the cathode or anode can be in contact with the substrate. The substrate can be a complex structure comprising multiple layers of materials. This is typically the case for active matrix substrates wherein TFTs are provided below the OLED layers. It is still necessary that the substrate, at least in the emissive pixilated areas, be comprised of largely transparent materials. The electrode in contact with the substrate is conveniently referred to as the bottom electrode. Conventionally, the bottom electrode is the anode, but is not limited to that configuration. The substrate can either be light transmissive or opaque, depending on the intended direction of light emission. The light transmissive property is desirable for viewing the EL emission through the substrate. Transparent glass or plastic is commonly employed in such cases. For applications where the EL emission is viewed through the top electrode, the transmissive characteristic of the bottom support can be light transmissive, light absorbing or light reflective. Substrates for use in this case include, but are not limited to, glass, plastic, semiconductor materials, silicon, ceramics, and circuit board materials. It is necessary to provide in these device configurations a light-transparent top electrode.

Anode

When the desired electroluminescent light emission (EL) is viewed through the anode, the anode 103 should be transparent or substantially transparent to the emission of interest. Common transparent anode materials used in are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Hole-Injecting Layer (HIL)

A hole injecting layer 105 may be provided between the anode and the hole transporting layer. The hole injecting layer may include more than one injecting compound, deposited as a blend or divided into separate layers. The hole injecting material can serve to improve the film formation property of subsequent organic layers and to adjust or facilitate injection of holes into the hole transporting layer. Suitable materials for use in the hole injecting layer include, but are not limited to, porphyrinic compounds as described in U.S. Pat. No. 4,720,432, plasma-deposited fluorocarbon polymers as described in U.S. Pat. No. 6,127,004, U.S. Pat. No. 6,208,075 and U.S. Pat. No. 6,208,077, some aromatic amines, for example, MTDATA (4,4',4"-tris[(3-methylphenyl)phenylamino]triphenylamine), and inorganic oxides including vanadium oxide (VOx), molybdenum oxide (MoOx), and nickel oxide (NiOx). Alternative hole injecting materials reportedly useful in organic EL devices are described in EP0891121, EP1029909, U.S. Pat. No. 6,720,573.

The thickness of a hole injecting layer containing a plasma-deposited fluorocarbon polymer can be in the range of 0.2 nm to 15 nm and suitably in the range of 0.3 to 1.5 nm.

Hole-Transporting Layer (HTL)

It is usually advantageous to have a hole transporting layer 107 deposited between the anode and the emissive layer. A hole transporting material deposited in said hole transporting layer between the anode and the light emitting layer may be the same or different from a hole transporting compound used as a co-host or in exciton blocking layer. The hole transporting layer may optionally include a hole injecting layer. The hole transporting layer may include more than one hole transporting compound, deposited as a blend or divided into separate layers.

The hole transporting layer contains at least one hole transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al U.S. Pat. No. 3,567,450 and U.S. Pat. No. 3,658,520.

A more preferred class of aromatic tertiary amines is those which include at least two aromatic tertiary amine moieties as described in U.S. Pat. No. 4,720,432 and U.S. Pat. No. 5,061,569. Such compounds include those represented by structural formula (HT1):

(HT1)

wherein $Q_1$ and $Q_2$ are independently selected aromatic tertiary amine moieties, and G is a linking group such as an arylene, cycloalkylene, or alkylene group of a carbon to carbon bond. In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural formula (HT1) and containing two triarylamine moieties is represented by structural formula (HT2):

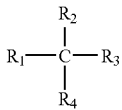
(HT2)

wherein $R_1$ and $R_2$ each independently represents a hydrogen atom, an aryl group, or an alkyl group or $R_1$ and $R_2$ together represent the atoms completing a cycloalkyl group; and $R_3$ and $R_4$ each independently represents an aryl group, which is in turn substituted with a diaryl substituted amino group, as indicated by structural formula (HT3):

(HT3)

wherein $R_5$ and $R_6$ are independently selected aryl groups. In one embodiment, at least one of $R_5$ or $R_6$ contains a polycyclic fused ring structure, e.g., a naphthalene.

Another class of aromatic tertiary amines is the tetraaryldiamines. Desirable tetraaryldiamines include two diarylamino groups, such as indicated by formula (HT3), linked through an arylene group. Useful tetraaryldiamines include those represented by formula (HT4):

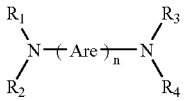
(HT4)

wherein each Are is an independently selected arylene group, such as a phenylene or anthracene moiety, n is an integer of from 1 to 4, and $R_1$, $R_2$, $R_3$, and $R_4$ are independently selected aryl groups. In a typical embodiment, at least one of $R_1$, $R_2$, $R_3$, and $R_4$ is a polycyclic fused ring structure, e.g., a naphthalene.

The various alkyl, alkylene, aryl, and arylene moieties of the foregoing structural formulae (HT1), (HT2), (HT3), (HT4) can each in turn be substituted. Typical substituents include alkyl groups, alkoxy groups, aryl groups, aryloxy groups, and halide such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, such as cyclopentyl, cyclohexyl, and cycloheptyl ring structures. The aryl and arylene moieties are usually phenyl and phenylene moieties.

The hole transporting layer can be formed of a single tertiary amine compound or a mixture of such compounds. Specifically, one may employ a triarylamine, such as a triarylamine satisfying the formula (HT2), in combination with a tetraaryldiamine, such as indicated by formula (HT4). Illustrative of useful aromatic tertiary amines are the following:

1,1-Bis(4-di-p-tolylaminophenyl)cyclohexane (TAPC);
1,1-Bis(4-di-p-tolylaminophenyl)-4-phenylcyclohexane;
N,N,N',N'-tetraphenyl-4,4'''-diamino-1,1':4',1'':4'',1'''-quaterphenyl;
Bis(4-dimethylamino-2-methylphenyl)phenylmethane;
Bis(4-diethylamino-2-methylphenyl)(4-methylphenyl) methane (MPMP);
1,4-bis[2-[4-[N,N-di(p-tolyl)amino]phenyl]vinyl]benzene (BDTAPVB);
N,N,N',N'-Tetra-p-tolyl-4,4'-diaminobiphenyl;
N,N,N',N'-Tetraphenyl-4,4'-diaminobiphenyl;
N,N,N',N'-tetra-1-naphthyl-4,4'-diaminobiphenyl;
N,N,N',N'-tetra-2-naphthyl-4,4'-diaminobiphenyl;
4,4'-Bis[N-(1-naphthyl)-N-phenylamino]biphenyl (NPB);
4,4'-Bis[N-(3-methylphenyl)-N-phenylamino]biphenyl (TPD);
4,4'-Bis [N-(1-naphthyl)-N-(2-naphthyl)amino]biphenyl (TNB);
4,4'-Bis[N-(1-naphthyl)-N-phenylamino]$_p$-terphenyl;
4,4'-Bis[N-(2-naphthyl)-N-phenylamino]biphenyl;
4,4'-Bis[N-(3-acenaphthenyl)-N-phenylamino]biphenyl;
1,5-Bis [N-(1-naphthyl)-N-phenylamino]naphthalene;
4,4'-Bis[N-(9-anthryl)-N-phenylamino]biphenyl;
4,4'-Bis[N-(1-anthryl)-N-phenylamino]-p-terphenyl;
4,4'-Bis[N-(2-phenanthryl)-N-phenylamino]biphenyl;
4,4'-Bis[N-(8-fluoranthenyl)-N-phenylamino]biphenyl;
4,4'-Bis[N-(2-pyrenyl)-N-phenylamino]biphenyl;
4,4'-Bis[N-(2-naphthacenyl)-N-phenylamino]biphenyl;
4,4'-Bis[N-(2-perylenyl)-N-phenylamino]biphenyl;
4,4'-Bis [N-(1-coronenyl)-N-phenylamino]biphenyl;
2,6-Bis(di-p-tolylamino)naphthalene;
2,6-Bis[di-(1-naphthyl)amino]naphthalene;
2,6-Bis[N-(1-naphthyl)-N-(2-naphthyl)amino]naphthalene;
N,N,N',N'-Tetra(2-naphthyl)-4,4''-diamino-p-terphenyl;
4,4'-Bis {N-phenyl-N-[4-(1-naphthyl)-phenyl] amino}biphenyl;
2,6-Bis[N,N-di(2-naphthyl)amino]fluorene;
4,4',4''-tris[(3-methylphenyl)phenylamino]triphenylamine (MTDATA);
N,N-bis[2,5-dimethyl-4-[(3-methylphenyl)phenylamino] phenyl]-2,5-dimethyl-N'-(3-methylphenyl)-N'-phenyl-1,4-benzenediamine;
4-(9H-carbazol-9-yl)-N,N-bis[4-(9H-carbazol-9-yl)phenyl]-benzenamine (TCTA);
4-(3-phenyl-9H-carbazol-9-yl)-N,N-bis[4(3-phenyl-9H-carbazol-9-yl)phenyl]-benzenamine;
9,9'-(2,2'-dimethyl[1,1'-biphenyl]-4,4'-diyl)bis-9H-carbazole (CDBP);
9,9'-[1,1'-biphenyl]-4,4'-diylbis-9H-carbazole (CBP);
9,9'-(1,3-phenylene)bis-9H-carbazole (mCP);
9-[4-(9H-carbazol-9-yl)phenyl]-N,N-diphenyl-9H-carbazol-3-amine;
9,9'-(1,4-phenylene)bis[N,N-diphenyl-9H-carbazol-3-amine;
9-[4-(9H-carbazol-9-yl)phenyl]-N,N,N',N'-tetraphenyl-9H-carbazole-3,6-diamine.

Another class of useful hole transporting materials includes polycyclic aromatic compounds as described in EP1009041. Some hole injecting materials described in EP0891121 and EP1029909, can also make useful hole transporting materials. In addition, polymeric hole transporting materials can be used including poly(N-vinylcarbazole) (PVK), polythiophenes, polypyrrole, polyaniline, and copolymers including poly(3,4-ethylenedioxythiophene)/ poly(4-styrenesulfonate) also called PEDOT/PSS.

Exciton/Electron Blocking Layer

An OLED device may include one or more exciton/electron blocking layers, 108 (FIG. 1), placed adjacent the light emitting layer 109 on the anode side, to help confine triplet excitons to the light emitting layer. For the exciton blocking layer to be capable of confining triplet excitons, the material or materials of this layer should have triplet energies greater than or equal to the triple energies of the phosphorescent emitter. If the triplet energy level of any material in the layer adjacent the light emitting layer is lower than that of the phosphorescent emitter, often that material will quench excited states in the light emitting layer, decreasing device luminous efficiency. In a preferred embodiment, the exciton/electron blocking layer also helps to confine electron-hole recombination events to the light emitting layer by blocking the escape of electrons from the light emitting layer into the exciton blocking layer. In order for the exciton blocking layer to have this electron blocking property, the material of this layer should have a lowest unoccupied molecular orbital (LUMO) energy level that is greater than that of the host material in the light emitting layer by at least 0.2 eV. In an embodiment wherein the host comprises a mixture of host materials, the LUMO energy level of the exciton blocking layer should be greater by at least 0.2 eV than that of the host material having the lowest LUMO energy level in order to have the preferred electron blocking property.

The relative energy levels of the highest occupied molecular orbital (HOMO) and the LUMO of materials may be estimated by several methods known in the art. When comparing energy levels of two materials, it is important to use estimated energy levels obtained by a single method for the HOMOs and a single method for the LUMOs, but it is not necessary to use the same method for both the HOMOs and the LUMOs. Two methods for estimating the HOMO energy level include measuring the ionization potential of the material by ultraviolet photoelectron spectroscopy and measuring the oxidation potential by an electrochemical technique such as cyclic voltammetry. The LUMO energy level may then be estimated by adding the optical band gap energy to the previously determined HOMO energy level. The energy difference between the LUMO and the HOMO is estimated to be the optical band gap. The relative LUMO energy levels of materials may also be estimated from reduction potentials of the materials measured in solution by an electrochemical technique such as cyclic voltammetry.

We have found that luminous yield and power efficiency in the OLED device employing a phosphorescent emitter in the light emitting layer can be improved significantly if the selected exciton blocking material or materials have a triplet energy greater or equal to 2.5 eV, especially for the case of green or blue-emitting phosphorescent emitters.

The exciton blocking layer is often between 1 and 500 nm thick and suitably between 10 and 300 nm thick. Thicknesses in this range are relatively easy to control in manufacturing. In addition to having high triplet energy, the exciton blocking layer 108 must be capable of transporting holes to the light emitting layer 109. Exciton blocking layer 108 can be used alone or with a hole transporting layer 107. The exciton blocking layer may include more than one compound, deposited as a blend or divided into separate sublayers. A hole transporting material deposited in the exciton blocking layer between the anode and the light emitting layer may be the same or different from the hole transporting compound used as a host or co-host. The exciton blocking material can comprise compounds containing one or more triarylamine groups, provided that their triplet energy exceeds that of the phosphorescent material. In a preferred embodiment of devices with emission green or blue light, the triplet energy of all materials in the exciton blocking layer is greater or equal to 2.5 eV. To meet the triplet energy requirement for the preferred embodiment of 2.5 eV or greater, said compounds should not contain aromatic hydrocarbon fused rings (e.g., a naphthalene group).

The substituted triarylamines that function as the exciton blocking material may be selected from compounds having the chemical formula (EBF-1):

(EBF-1)

In formula (EBF-1), Are is independently selected from alkyl, substituted alkyl, aryl, or substituted aryl group;

$R_1$-$R_4$ are independently selected aryl groups;

n is an integer of from 1 to 4.

In a preferred embodiment, Are and $R_1$-$R_4$ do not include aromatic hydrocarbon fused rings.

Example materials useful in the exciton blocking layer 108 include, but are not limited to:

2,2'-dimethyl-N,N,N',N'-tetrakis(4-methylphenyl)-1,1'-biphenyl-4,4'-diamine;

4,4',4''-tris[(3-methylphenyl)phenylamino]triphenylamine (MTDATA);

4,4',4''-tris(N,N-diphenyl-amino)triphenylamine (TDATA);

N,N-bis[2,5-dimethyl-4-[(3-methylphenyl)phenylamino]phenyl]-2,5-dimethyl-N'-(3-methylphenyl)-N'-phenyl-1,4-benzenediamine; and tetraphenyl-p-phenylenediamine (TPPD);

Bis[4-(N,N-diethylamino)-2-methylphenyl](4-methylpenyl)methane;

Bis[4-(N,N-diethylamino)-2-methylphenyl](4-methylphenyl)ethane;

(4-Diethylaminophenyl)triphenylmethane;

Bis(4-diethylaminophenyl)diphenylmethane.

In one desirable embodiment the material in the exciton blocking layer is selected from formula (EBF-2):

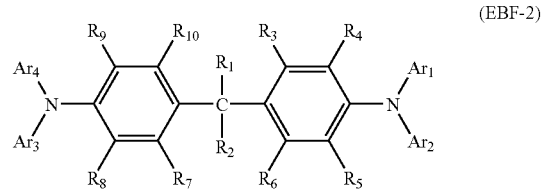

(EBF-2)

In formula (EBF-2), $R_1$ and $R_2$ represent substituents, provided that $R_1$ and $R_2$ can join to form a ring. For example, $R_1$ and $R_2$ can be methyl groups or join to form a cyclohexyl ring. $Ar_1$-$Ar_4$ represent independently selected aromatic groups, for example phenyl groups or tolyl groups. $R_3$-$R_{10}$ independently represent hydrogen, alkyl, substituted alkyl, aryl, substituted aryl group. In one desirable embodiment, $R_1$-$R_2$, $Ar_1$-$Ar_4$ and $R_3$-$R_{10}$ do not contain fused aromatic rings.

Some non-limiting examples of such materials are:

1,1-Bis(4-(N,N-di-p-tolylamino)phenyl)cyclohexane (TAPC);

1,1-Bis(4-(N,N-di-p-tolylamino)phenyl)cyclopentane;

4,4'-(9H-fluoren-9-ylidene)bis[N,N-bis(4-methylphenyl)-benzenamine;

1,1-Bis(4-(N,N-di-p-tolylamino)phenyl)-4-phenylcyclohexane;
1,1-Bis(4-(N,N-di-p-tolylamino)phenyl)-4-methylcyclohexane;
1,1-Bis(4-(N,N-di-p-tolylamino)phenyl)-3-phenylpropane.

In one suitable embodiment the exciton blocking material comprises a material of formula (EBF-3):

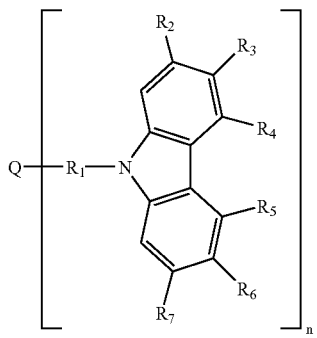

(EBF-3)

wherein n is an integer from 1 to 4;
Q is N, C, aryl, or substituted aryl group;
$R_1$ is phenyl, substituted phenyl, biphenyl, substituted biphenyl, aryl or substituted aryl;
$R_2$ through $R_7$ are independently hydrogen, alkyl, phenyl or substituted phenyl, aryl amine, carbazole, or substituted carbazole; provided that $R_2$-$R_7$ do not contain aromatic hydrocarbon fused rings.

Some non-limiting examples of such materials are:
4-(9H-carbazol-9-yl)-N,N-bis[4-(9H-carbazol-9-yl)phenyl]-benzenamine (TCTA);
4-(3-phenyl-9H-carbazol-9-yl)-N,N-bis[4(3-phenyl-9H-carbazol-9-yl)phenyl]-benzenamine;
9,9'-[5'-[4-(9H-carbazol-9-yl)phenyl][1,1':3',1''-terphenyl]-4,4''-diyl]bis-9H-carbazole.

In one suitable embodiment the exciton blocking material comprises a material of formula (EBF-4):

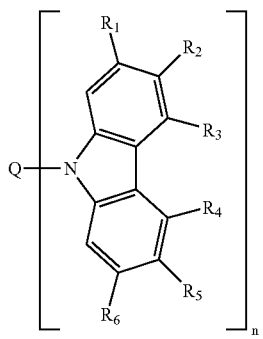

(EBF-4)

wherein n is an integer from 1 to 4;
Q is phenyl, substituted phenyl, biphenyl, substituted biphenyl, aryl, or substituted aryl group;
$R_1$ through $R_6$ are independently hydrogen, alkyl, phenyl or substituted phenyl, aryl amine, carbazole, or substituted carbazole;
provided that $R_1$-$R_6$ do not contain aromatic hydrocarbon fused rings.

Non-limiting examples of suitable materials are:
9,9'-(2,2'-dimethyl[1,1'-biphenyl]-4,4'-diyl)bis-9H-carbazole (CDBP);
9,9'-[1,1'-biphenyl]-4,4'-diylbis-9H-carbazole (CBP);
9,9'-(1,3-phenylene)bis-9H-carbazole (mCP);
9,9'-(1,4-phenylene)bis-9H-carbazole;
9,9',9''-(1,3,5-benzenetriyl)tris-9H-carbazole;
9,9'-(1,4-phenylene)bis[N,N,N',N'-tetraphenyl-9H-carbazole-3,6-diamine;
9-[4-(9H-carbazol-9-yl)phenyl]-N,N-diphenyl-9H-carbazol-3-amine;
9,9'-(1,4-phenylene)bis[N,N-diphenyl-9H-carbazol-3-amine;
9-[4-(9H-carbazol-9-yl)phenyl]-N,N,N',N'-tetraphenyl-9H-carbazole-3,6-diamine;
9-phenyl-9H-carbazole.

Metal complexes may also serve as exciton blocking layers as long as they have the desired triplet energies and hole transport and electron blocking properties. An example of this is, fac-tris(1-phenylpyrazolato-N,C2)iridium(III) (Ir(ppz)$_3$), as described in US 20030175553.

Light-Emitting Layer (LEL)

Suitably, the light-emitting layer of the OLED device comprises one or more host materials and one or more guest materials for emitting light. At least one of the guest materials is suitably a fluorescent or phosphorescent material. The light-emitting guest material(s) is usually present in an amount less than the amount of host materials and is typically present in an amount of up to 20 wt % of the host, more typically from 0.1-10 wt % of the host. For convenience, the light-emitting guest material may be referred to as a light emitting dopant. A phosphorescent guest material may be referred to herein as a phosphorescent material, or phosphorescent dopant. The phosphorescent material is preferably a low molecular weight compound, but it may also be an oligomer or a polymer. It may be provided as a discrete material dispersed in the host material, or it may be bonded in some way to the host material, for example, covalently bonded into a polymeric host.

Fluorescent materials may be used in the same layer as the phosphorescent material, in adjacent layers, in non-adjacent layers, in adjacent pixels, or any combination. Care must be taken to select materials that will not adversely affect the performance of the phosphorescent materials in an OLED device. One skilled in the art will understand that concentrations and triplet energies of materials in the same layer as the phosphorescent material or in an adjacent layer must be appropriately set so as to prevent unwanted quenching of the phosphorescence.

Host Materials for Phosphorescent Materials

Suitable host materials have a triplet energy (the difference in energy between the lowest triplet excited state and the singlet ground state of the host) that is greater than or equal to the triplet energy of the phosphorescent emitter. This energy level condition is necessary so that triplet excitons are transferred to the phosphorescent emitter molecules, and any triplet excitons formed directly on the phosphorescent emitter molecules remain until emission occurs. However, efficient emission from devices in which the host material has a lower triplet energy than the phosphorescent emitter is still possible in some cases as reported by C. Adachi, et al. *Appl. Phys. Lett.*, 79, 2082-2084 (2001). Triplet energy is conveniently measured by any of several means, as discussed for instance in S. L. Murov, I. Carmichael, and G. L. Hug, *Handbook of Photochemistry*, 2nd ed. (Marcel Dekker, New York, 1993).

In the absence of experimental data the triplet energies may be estimated in the following manner. The triplet state energy for a molecule is defined as the difference between the ground state energy (E(gs)) of the molecule and the energy of the lowest triplet state (E(ts)) of the molecule, both given in eV. These energies can be calculated using the B3LYP method as implemented in the Gaussian98 (Gaussian, Inc., Pittsburgh, Pa.) computer program. The basis set for use with the B3LYP method is defined as follows: MIDI! for all atoms for which MIDI! is defined, 6-31G* for all atoms defined in 6-31 G* but not in MIDI!, and either the LACV3P or the LANL2DZ basis set and pseudopotential for atoms not defined in MIDI! or 6-31G*, with LACV3P being the preferred method. For any remaining atoms, any published basis set and pseudopotential may be used. MIDI!, 6-31 G* and LANL2DZ are used as implemented in the Gaussian98 computer code and LACV3P is used as implemented in the Jaguar 4.1 (Schrodinger, Inc., Portland Oreg.) computer code. The energy of each state is computed at the minimum-energy geometry for that state. The difference in energy between the two states is further modified by Equation 1 to give the triplet state energy (E(t)):

$$E(t)=0.84*(E(ts)-E(gs))+0.35 \quad (1)$$

For polymeric or oligomeric materials, it is sufficient to compute the triplet energy over a monomer or oligomer of sufficient size so that additional units do not substantially change the computed triplet energy of the material.

Desirable host materials are capable of forming a continuous film. The light emitting layer may contain more than one host material in order to improve the device's film morphology, electrical properties, light emission efficiency, and lifetime. Suitable host materials are described in WO00/70655; WO01/39234; WO01/93642; WO02/074015; WO02/15645, and US20020117662.

Types of triplet host materials may be categorized according to their charge transport properties. The two major types are those that are predominantly electron transporting and those that are predominantly hole transporting. It should be noted that some host materials which may be categorized as transporting dominantly one type of charge, may transport both types of charges, especially in certain device structures, for example CBP which is described in C. Adachi, R. Kwong, and S. R. Forrest, *Organic Electronics*, 2, 37-43 (2001). Another type of host are those having a wide energy gap between the HOMO and LUMO such that they do not readily transport charges of either type and instead rely on charge injection directly into the phosphorescent dopant molecules.

A desirable electron transporting host may be any suitable electron transporting compound, such as benzazole, phenanthroline, 1,3,4-oxadiazole, triazole, triazine, or triarylborane, as long as it has a triplet energy that is higher than that of the phosphorescent emitter to be employed.

A preferred class of benzazoles is described by Jianmin Shi et al. in U.S. Pat. No. 5,645,948 and U.S. Pat. No. 5,766,779. Such compounds are represented by structural formula (PHF-1):

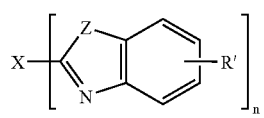
(PHF-1)

In formula (PHF-1), n is selected from 2 to 8;
Z is independently O, NR or S;

R and R' are individually hydrogen; alkyl of from 1 to 24 carbon atoms, for example, propyl, t-butyl, heptyl, and the like; aryl or hetero-atom substituted aryl of from 5 to 20 carbon atoms, for example, phenyl and naphthyl, furyl, thienyl, pyridyl, quinolinyl and other heterocyclic systems; or halo such as chloro, fluoro; or atoms necessary to complete a fused aromatic ring; and X is a linkage unit consisting of carbon, alkyl, aryl, substituted alkyl, or substituted aryl, which conjugately or unconjugately connects the multiple benzazoles together.

An example of a useful benzazole is 2,2',2"-(1,3,5-phenylene)tris[1-phenyl-1H-benzimidazole] (TPBI) represented by a formula (PHF-2) shown below:

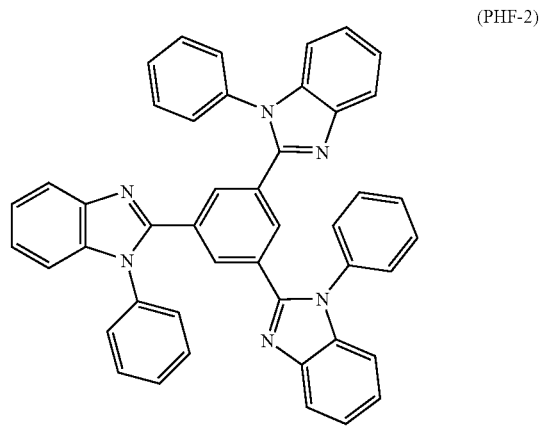
(PHF-2)

Another class of the electron transporting materials suitable for use as a host includes various substituted phenanthrolines as represented by formula (PHF-3):

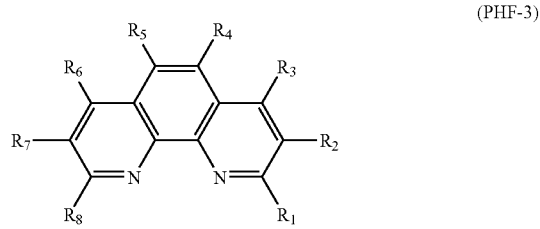
(PHF-3)

In formula (PHF-3), $R_1$-$R_8$ are independently hydrogen, alkyl group, aryl or substituted aryl group, and at least one of $R_1$-$R_8$ is aryl group or substituted aryl group.

Examples of suitable materials are 2,9-dimethyl-4,7-diphenyl-1,10-phenanthroline (BCP) (see formula (PH-1)) and 4,7-diphenyl-1,10-phenanthroline (Bphen) (see formula (PH-2)).

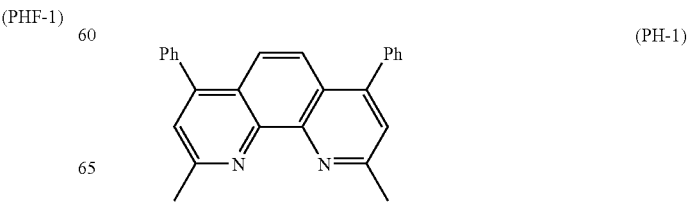
(PH-1)

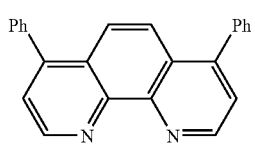
(PH-2)

A triarylborane that functions as an electron transporting host may be selected from compounds having the chemical formula (PHF-4):

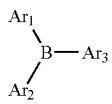
(PHF-4)

wherein $Ar_1$ to $Ar_3$ are independently an aromatic hydrocarbocyclic group or an aromatic heterocyclic group which may have one or more substituent. It is preferable that compounds having the above structure are selected from formula (PHF-5):

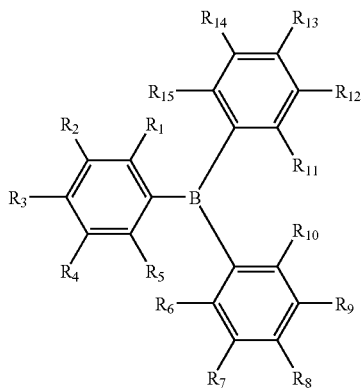
(PHF-5)

wherein $R_1$-$R_{15}$ are independently hydrogen, fluoro, cyano, trifluoromethyl, sulfonyl, alkyl, aryl or substituted aryl group.

Specific representative embodiments of the triarylboranes include:

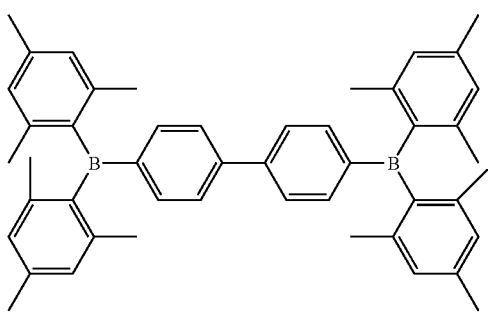
(PH-3)

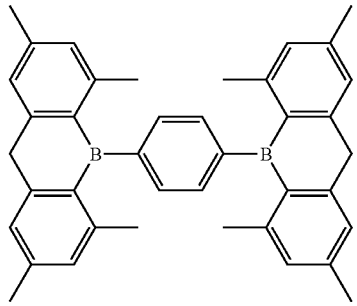
(PH-4)

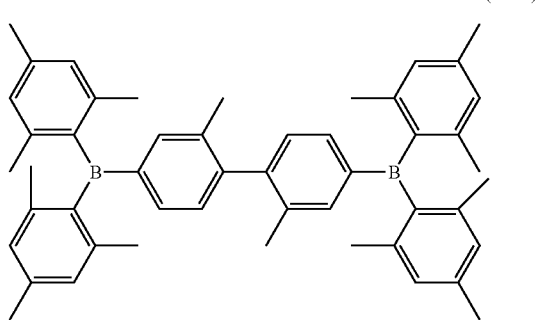
(PH-5)

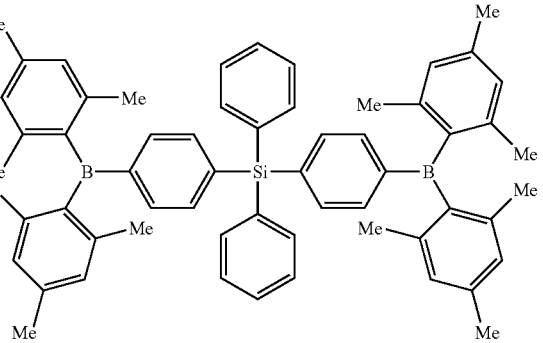
(PH-6)

An electron transporting host may be selected from substituted 1,3,4-oxadiazoles. Illustrative of the useful substituted oxadiazoles are the following:

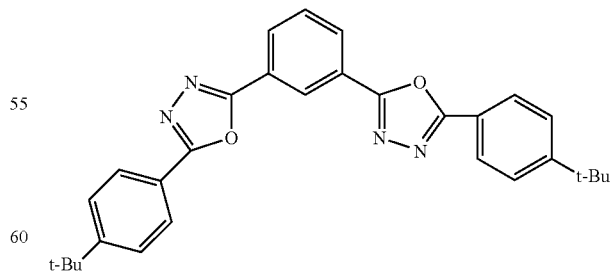
(PH-8)

An electron transporting host may be selected from substituted 1,2,4-triazoles. An example of a useful triazole is 3-phenyl-4-(1-naphthyl)-5-phenyl-1,2,4-triazole represented by formula (PHF-6):

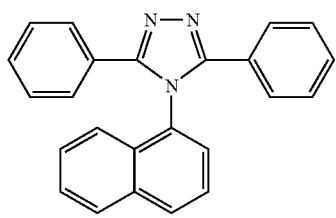
(PHF-6)

The electron transporting host may be selected from substituted 1,3,5-triazines. Examples of suitable materials are:
2,4,6-tris(diphenylamino)-1,3,5-triazine;
2,4,6-tricarbazolo-1,3,5-triazine;
2,4,6-tris(N-phenyl-2-naphthylamino)-1,3,5-triazine;
2,4,6-tris(N-phenyl-1-naphthylamino)-1,3,5-triazine;
4,4',6,6'-tetraphenyl-2,2'-bis-1,3,5-triazine;
2,4,6-tris([1,1':3',1''-terphenyl]-5'-yl)-1,3,5-triazine.

In one embodiment, a suitable host material is an aluminum or gallium complex. Particularly useful hosts materials are represented by Formula (PHF-7).

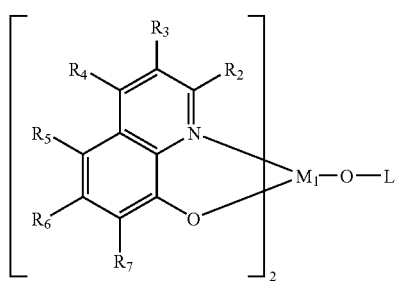
(PHF-7)

In Formula (PHF-7), $M_1$ represents Al or Ga. $R_2$-$R_7$ represent hydrogen or an independently selected substituent. Desirably, $R_2$ represents an electron-donating group, such as a methyl group. Suitably, $R_3$ and $R_4$ each independently represent hydrogen or an electron-donating group. Preferably, $R_5$, $R_6$, and $R_7$ each independently represent hydrogen or an electron-accepting group. Adjacent substituents, $R_2$-$R_7$, may combine to form a ring group. L is an aromatic moiety linked to the aluminum by oxygen, which may be substituted with substituent groups such that L has from 6 to 30 carbon atoms. Illustrative examples of Formula (PHF-7) materials are listed below.

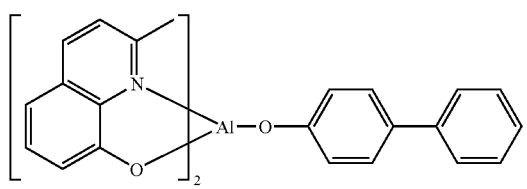
(PH-9)

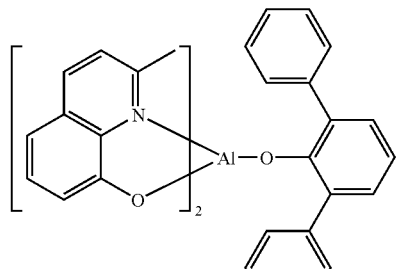
(PH-10)

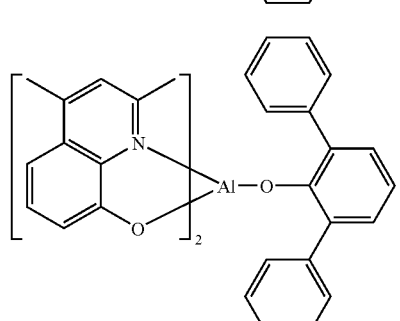
(PH-11)

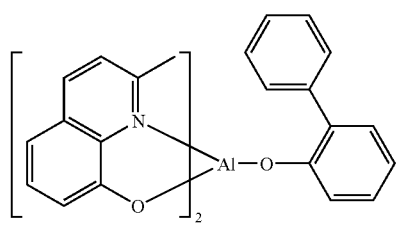
(PH-12)

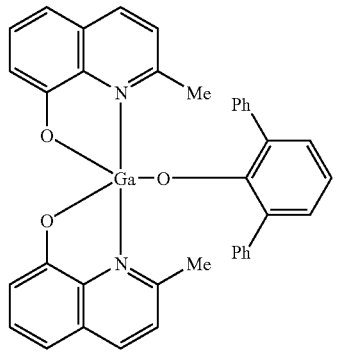
(PH-13)

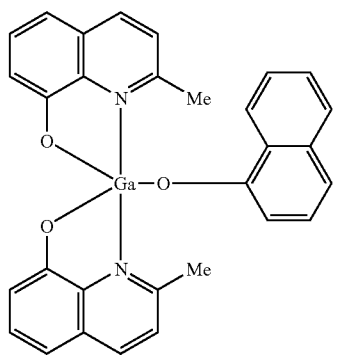
(PH-14)

-continued

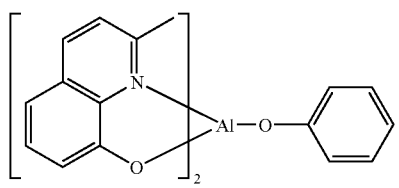
(PH-15)

A desirable hole transporting host may be any suitable hole transporting compound, such as a triarylamine or a carbazole, as long it has a triplet energy higher than that of the phosphorescent emitter to be employed. A suitable class of hole transporting compounds for use as a host are aromatic tertiary amines. These compounds contain at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. in U.S. Pat. No. 3,180,730. Other suitable triarylamines substituted with one or more vinyl radicals and/or comprising at least one active hydrogen containing group are disclosed by Brantley et al. in U.S. Pat. No. 3,567,450 and U.S. Pat. No. 3,658,520.

A preferred class of aromatic tertiary amines are those which include at least two aromatic tertiary amine moieties as described in U.S. Pat. No. 4,720,432 and U.S. Pat. No. 5,061,569. Desirable tetraaryldiamines include two diarylamino groups, such as indicated by formula (PHF-8):

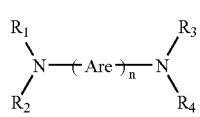
(PHF-8)

wherein each Are is an independently selected arylene group, such as a phenylene or anthracene moiety, n is selected from 1 to 4, and $R_1$-$R_4$ are independently selected aryl groups.

In a typical embodiment, at least one of $R_1$-$R_4$ is a polycyclic fused ring structure, e.g., a naphthalene. However, when the emission of the dopant is blue or green in color it is less preferred for an aryl amine host material to have a polycyclic fused ring substituent.

Representative examples of the useful compounds include the following:

4,4'-Bis[N-(1-naphthyl)-N-phenylamino]biphenyl (NPB);
4,4'-Bis [N-(1-naphthyl)-N-(2-naphthyl)amino]biphenyl (TNB);
4,4'-Bis[N-(3-methylphenyl)-N-phenylamino]biphenyl (TPD);
4,4'-Bis-diphenylamino-terphenyl;
2,6,2',6'-tetramethyl-N,N,N',N'-tetraphenyl-benzidine;
4,4',4''-tris[(3-methylphenyl)phenylamino]triphenylamine (MTDATA);
4,4',4''-tris(N,N-diphenyl-amino)triphenylamine (TDATA);
N,N-bis[2,5-dimethyl-4-[(3-methylphenyl)phenylamino] phenyl]-2,5-dimethyl-N'-(3-methylphenyl)-N'-phenyl-1, 4-benzenediamine.

In one desirable embodiment the hole transporting host comprises a material of formula (PHF-9):

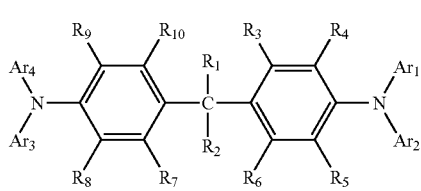
(PHF-9)

In formula (PHF-9), $R_1$ and $R_2$ represent substituents, provided that $R_1$ and $R_2$ can join to form a ring. For example, $R_1$ and $R_2$ can be methyl groups or join to form a cyclohexyl ring;

$Ar_1$-$Ar_4$ represent independently selected aromatic groups, for example phenyl groups or tolyl groups;

$R_3$-$R_{10}$ independently represent hydrogen, alkyl, substituted alkyl, aryl, substituted aryl group.

Examples of suitable materials include, but are not limited to:

1,1-Bis(4-(N,N-di-p-tolylamino)phenyl)cyclohexane (TAPC);
1,1-Bis(4-(N,N-di-p-tolylamino)phenyl)cyclopentane;
4,4'-(9H-fluoren-9-ylidene)bis[N,N-bis(4-methylphenyl)-benzenamine;
1,1-Bis(4-(N,N-di-p-tolylamino)phenyl)-4-phenylcyclohexane;
1,1-Bis(4-(N,N-di-p-tolylamino)phenyl)-4-methylcyclohexane;
1,1-Bis(4-(N,N-di-p-tolylamino)phenyl)-3-phenylpropane;
Bis[4-(N,N-diethylamino)-2-methylphenyl](4-methylphenyl)methane;
Bis[4-(N,N-diethylamino)-2-methylphenyl](4-methylphenyl)ethane;
(4-Diethylaminophenyl)triphenylmethane;
Bis(4-diethylaminophenyl)diphenylmethane.

A useful class of compounds for use as the hole transporting host includes carbazole derivatives such as those represented by formula (PHF-10):

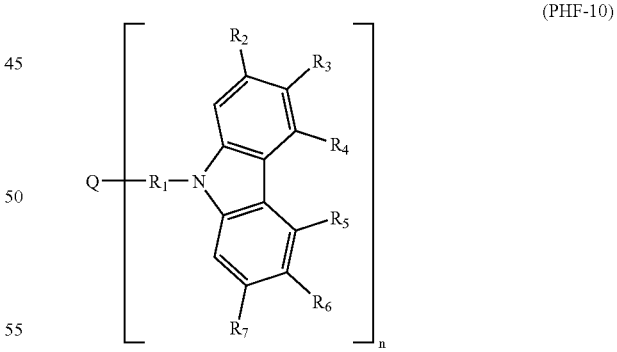
(PHF-10)

In formula (PHF-10), Q independently represents nitrogen, carbon, silicon, a substituted silicon group, an aryl group, or substituted aryl group, preferably a phenyl group;

$R_1$ is preferably an aryl or substituted aryl group, and more preferably a phenyl group, substituted phenyl, biphenyl, substituted biphenyl group;

$R_2$ through $R_7$ are independently hydrogen, alkyl, phenyl or substituted phenyl group, aryl amine, carbazole, or substituted carbazole;

and n is selected from 1 to 4.

Illustrative useful substituted carbazoles are the following:
4-(9H-carbazol-9-yl)-N,N-bis[4-(9H-carbazol-9-yl)phenyl]-benzenamine (TCTA);
4-(3-phenyl-9H-carbazol-9-yl)-N,N-bis[4(3-phenyl-9H-carbazol-9-yl)phenyl]-benzenamine;
9,9'-[5'-[4-(9H-carbazol-9-yl)phenyl][1,1':3',1''-terphenyl]-4,4''-diyl]bis-9H-carbazole;
3,5-bis(9-carbazolyl)tetraphenylsilane (SimCP).

In one suitable embodiment the hole transporting host comprises a material of formula (PHF-11):

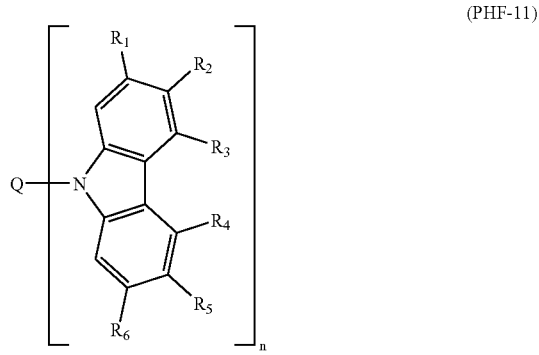

(PHF-11)

In formula (PHF-11), n is selected from 1 to 4;
Q independently represents phenyl group, substituted phenyl group, biphenyl, substituted biphenyl group, aryl, or substituted aryl group;
$R_1$ through $R_6$ are independently hydrogen, alkyl, phenyl or substituted phenyl, aryl amine, carbazole, or substituted carbazole.

Examples of suitable materials are the following:
9,9'-(2,2'-dimethyl[1,1'-biphenyl]-4,4'-diyl)bis-9H-carbazole (CDBP);
9,9'-[1,1'-biphenyl]-4,4'-diylbis-9H-carbazole (CBP);
9,9'-(1,3-phenylene)bis-9H-carbazole (mCP);
9,9'-(1,4-phenylene)bis-9H-carbazole;
9,9',9''-(1,3,5-benzenetriyl)tris-9H-carbazole;
9,9'-(1,4-phenylene)bis[N,N,N',N'-tetraphenyl-9H-carbazole-3,6-diamine;
9-[4-(9H-carbazol-9-yl)phenyl]-N,N-diphenyl-9H-carbazol-3-amine;
9,9'-(1,4-phenylene)bis[N,N-diphenyl-9H-carbazol-3-amine;
9-[4-(9H-carbazol-9-yl)phenyl]-N,N,N',N'-tetraphenyl-9H-carbazole-3,6-diamine.

Host materials which are electron transporting or hole transporting with some electron transporting properties, such as carbazoles, are generally more desirable when used as a single host material. This is especially true for typical phosphorescent dopants that are hole-trapping or capable of accepting injected holes. Less preferable are host materials which are primarily hole transporting and have little electron transporting properties, such as triarlyamines. Injecting electrons into these latter hole transporting hosts may be difficult because of their relatively high LUMO energies.

Host materials may comprise a mixture of two or more host materials. Particularly useful is a mixture comprising at least one each of an electron transporting and a hole transporting co-host. The optimum concentration of the hole transporting co-host(s) may be determined by experimentation and may be within the range 10 to 90 weight % of the total of the hole- and electron transporting co-host materials in the light emitting layer, and is often found to be in the range 15 to 30 wt. %. It is further noted that electron-transporting molecules and hole-transporting molecules may be covalently joined together to form single host molecules having both electron-transporting and hole-transporting properties.

A wide energy gap host material may be any suitable compound having a large HOMO-LUMO gap such that the HOMO and LUMO of the phosphorescent emissive material are within the gap between the HOMO and LUMO for the host. In this case, the phosphorescent emissive material acts as the primary charge carrier for both electrons and holes, as well as the site for the trapping of excitons. Often the phosphorescent dopants for use with the wide energy gap hosts are selected to have electron-withdrawing substituents to facilitate electron injection. The "wide energy gap" host material functions as a non-charge carrying material in the system. Such a combination may lead to high operation voltage of the device, as the concentration of the charge-carrying dopant is typically below 10% in the emissive layer.

Thompson et al. disclosed in US 2004/0209115 and US 2004/0209116 a group of wide energy gap hosts having triplet energies suitable for blue phosphorescent OLEDs. Such compounds include those represented by structural formula (PHF-12):

(PHF-12)

wherein:

X is Si or Pb; $Ar_1$, $Ar_2$, $Ar_3$ and $Ar_4$ are each an aromatic group independently selected from phenyl and high triplet energy heterocyclic groups such as pyridine, pyrazole, thiophene, etc. It is believed that the HOMO-LUMO gaps in these materials is large due to the electronically isolated aromatic units, and the lack of any conjugating substituents.

Illustrative examples of this type of hosts include:

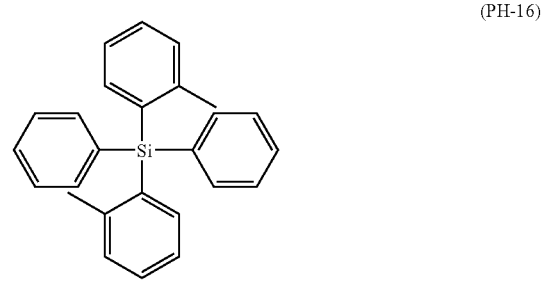

(PH-16)

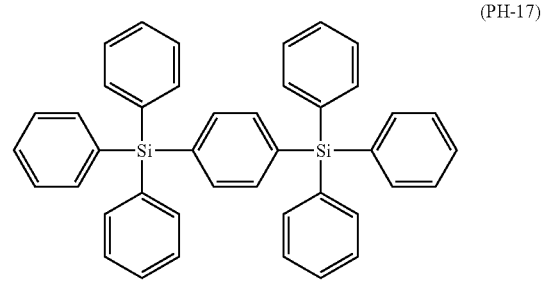

(PH-17)

(PH-18)

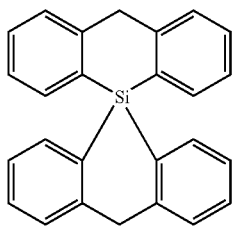

Phosphorescent Materials

The light emitting layer 109 of the EL device comprises one or more host materials and one or more phosphorescent guest materials. In combination to the previously described phosphorescent dopants, other dopants may be additionally used in the light emitting layer. The light emitting phosphorescent guest material(s) is typically present in an amount of from 1 to 20 by weight % of the light emitting layer, and conveniently from 2 to 8% by weight of the light emitting layer. In some embodiments, the phosphorescent guest material(s) may be attached to one or more host materials. For convenience, the phosphorescent complex guest material may be referred to herein as a phosphorescent material.

Additional useful phosphorescent materials are described by formula (PDF-1):

PDF-1

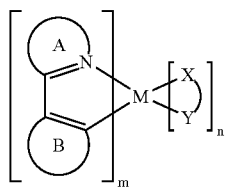

where A is a substituted or unsubstituted heterocyclic ring containing at least one N atom; B is a substituted or unsubstituted aromatic or heteroaromatic ring, or ring containing a vinyl carbon bonded to M; X—Y is an anionic bidentate ligand; m is an integer from 1 to 3 and n is an integer from 0 to 2 such that the sum of m and n is 3 when M is Rh or Ir; or m is an integer from 1 to 2 and n in an integer from 0 to 1 such that the sum of m and n is 2 when M is Pt or Pd.

Compounds according to Formula (PDF-1) may be referred to as C,N-cyclometallated complexes to indicate that the central metal atom is contained in a cyclic unit formed by bonding the metal atom to carbon and nitrogen atoms of one or more ligands. Examples of heterocyclic ring A in Formula (PDF-1) include substituted or unsubstituted pyridine, quinoline, isoquinoline, pyrimidine, pyrazine, indole, indazole, thiazole, and oxazole rings. Examples of ring B in Formula (PDF-1) include substituted or unsubstituted phenyl, napthyl, thienyl, benzothienyl, furanyl rings. Ring B in Formula (PDF-1) may also be a N-containing ring such as pyridine, with the proviso that the N-containing ring is bonded to M through a C atom as shown in Formula (PDF-1) and not through the N atom.

An example of a tris-C,N-cyclometallated complex according to Formula (PDF-1) with m=3 and n=0 is tris(2-phenyl-pyridinato-N,C$^{2'}$-)iridium(III), shown below in stereodiagrams as facial (fac-) or meridional (mer-) isomers.

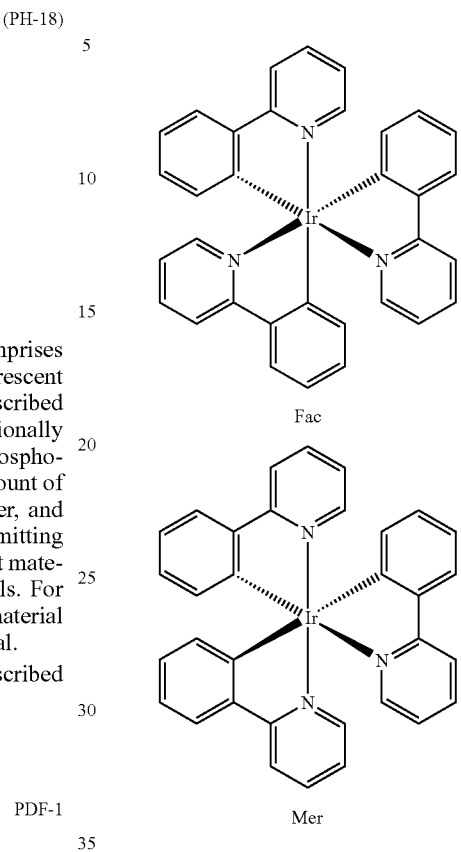

Generally, facial isomers are preferred since they are often found to have higher phosphorescent quantum yields than the meridional isomers. Additional examples of tris-C,N-cyclometallated phosphorescent materials according to Formula 1 are tris(2-(4'-methylphenyl)pyridinato-N,C$^{2'}$)iridium(III), tris(3-phenylisoquinolinato-N,C$^{2'}$)iridium(III), tris(2-phenylquinolinato-N,C$^{2'}$)iridium(III), tris(1-phenylisoquinolinato-N,C$^{2'}$)iridium(III), tris(1-(4'-methylphenyl)isoquinolinato-N,C$^{2'}$)iridium(III), tris(2-(4',6'-difluorophenyl)-pyridinato-N,C$^{2'}$)iridium(III), tris(2-(5'-phenyl-4',6'-difluorophenyl)-pyridinato-N,C$^{2'}$)Iridium(III), tris(2-(5'-phenyl-pyridinato-N,C$^{2'}$)Iridium(III), tris(2-(2'-benzothienyl)pyridinato-N,C$^{3'}$)iridium(III), tris(2-phenyl-3,3'-dimethyl)indolato-N,C$^{2'}$)iridium(III), and tris(1-phenyl-1H-indazolato-N,C$^{2'}$)iridium(III).

Tris-C,N-cyclometallated phosphorescent materials also include compounds according to Formula 1 wherein the monoanionic bidentate ligand X—Y is another C,N-cyclometallating ligand. Examples include bis(1-phenylisoquinolinato-N,C$^{2'}$)(2-phenylpyridinato-N,C$^{2'}$)iridium(III), bis(2-phenylpyridinato-N,C$^{2'}$) (1-phenylisoquinolinato-N,C$^{2'}$) iridium(III), bis(1-phenylisoquinolinato-N,C$^{2'}$)(2-phenyl-5-methyl-pyridinato-N,C$^{2'}$)iridium(III), bis(1-phenylisoquinolinato-N,C$^{2'}$)(2-phenyl-4-methyl-pyridinato-N,C$^{2'}$)iridium(III), and bis(1-phenylisoquinolinato-N,C$^{2'}$)(2-phenyl-3-methyl-pyridinato-N,C$^{2'}$)iridium(III).

Structural formulae of some tris-C,N-cyclometallated iridium complexes are shown below.

PD-1 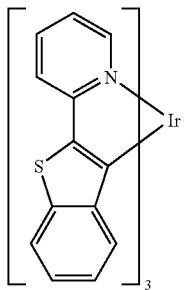
PD-2 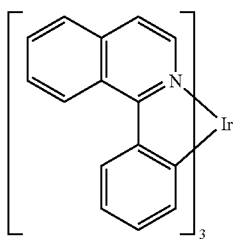
PD-3 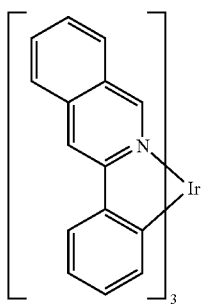
PD-4 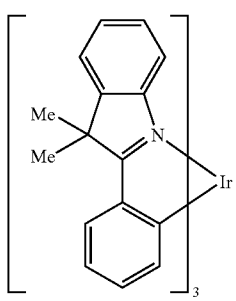
PD-5 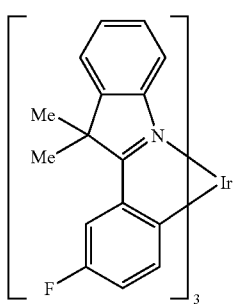
-continued
PD-6 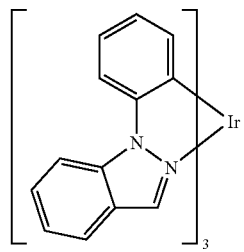
PD-7 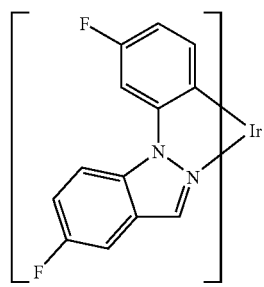
PD-8 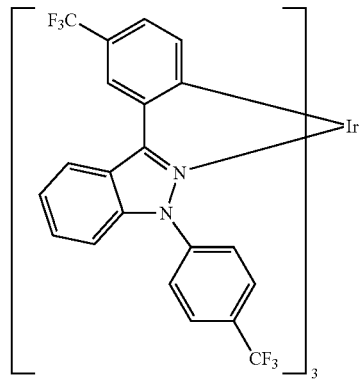
PD-9 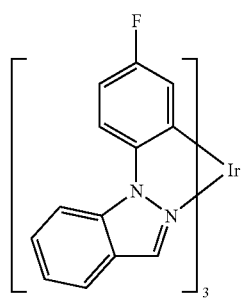
PD-10 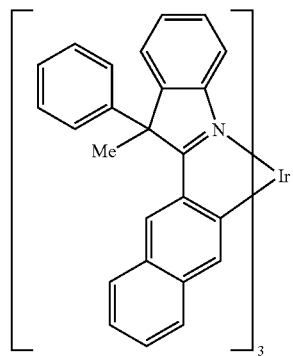

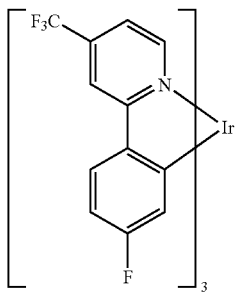

PD-11

Suitable phosphorescent materials according to Formula PDF-11 may in addition to the C,N-cyclometallating ligand(s) also contain monoanionic bidentate ligand(s) X—Y that are not C,N-cyclometallating. Common examples are beta-diketonates such as acetylacetonate, and Schiff bases such as picolinate. Examples of such mixed ligand complexes according to Formula 1 include bis(2-phenylpyridinato-N, $C^{2'}$)iridium(III)(acetylacetonate), bis(2-(2'-benzothienyl)pyridinato-N,$C^{3'}$)iridium(III)(acetylacetonate), and bis(2-(4',6'-difluorophenyl)-pyridinato-N,$C^{2'}$)iridium(III)(picolinate).

Other important phosphorescent materials according to Formula PDF-1 include C,N-cyclometallated Pt(II) complexes such as cis-bis(2-phenylpyridinato-N,$C^{2'}$)platinum (II), cis-bis(2-(2'-thienyl)pyridinato-N,$C^{3'}$) platinum(II), cis-bis(2-(2'-thienyl)quinolinato-N,$C^{5'}$) platinum(II), or (2-(4', 6'-difluorophenyl)pyridinato-N,$C^{2'}$) platinum (II) (acetylacetonate).

In addition to bidentate C,N-cyclometallating complexes represented by Formula PDF-1, many suitable phosphorescent emitters contain multidentate C,N-cyclometallating ligands. Phosphorescent emitters having tridentate ligands are disclosed in U.S. Pat. No. 6,824,895 and U.S. Ser. No. 10/729,238 and references therein, incorporated in their entirety herein by reference. Phosphorescent emitters having tetradentate ligands are described by the following formulae:

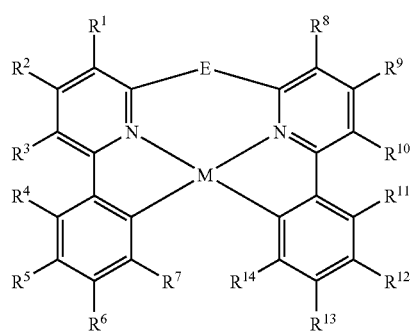

(PDF-2)

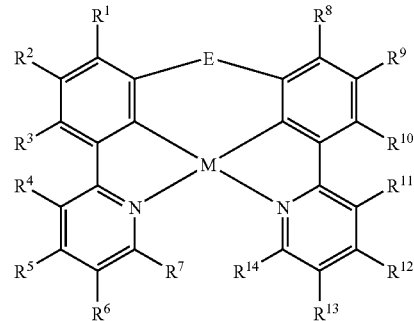

(PDF-3)

where M is Pt or Pd; $R^1$-$R^7$ represent hydrogen or independently selected substituents, provided that $R^1$ and $R^2$, $R^2$ and $R^3$, $R^3$ and $R^4$, $R^4$ and $R^5$, $R^5$ and $R^6$, as well as $R^6$ and $R^7$ may join to form a ring group; $R^8$-$R^{14}$ represent hydrogen or independently selected substituents, provided that $R^8$ and $R^9$, $R^9$ and $R^{10}$, $R^{10}$ and $R^{11}$, $R^{11}$ and $R^{12}$, $R^{12}$ and $R^{13}$, as well as $R^{13}$ and $R^{14}$ may join to form a ring group; E represents a bridging group selected from the following:

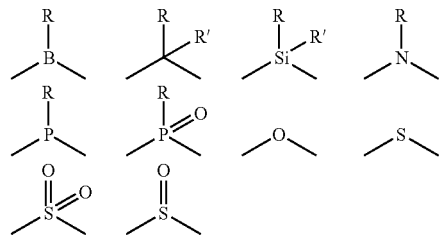

where R and R' represent hydrogen or independently selected substituents, provided R and R' may combine to form a ring group.

In one embodiment, the tetradentate C,N-cyclometallated phosphorescent emitter is represented by the following formula:

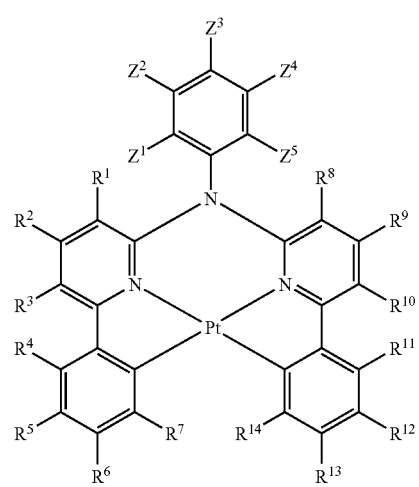

(PDF-4)

where, $R^1$-$R^7$ represent hydrogen or independently selected substituents, provided that $R^1$ and $R^2$, $R^2$ and $R^3$, $R^3$ and $R^4$, $R^4$ and $R^5$, $R^5$ and $R^6$, as well as $R^6$ and $R^7$ may combine to form a ring group; $R^8$-$R^{14}$ represent hydrogen or independently selected substituents, provided that $R^8$ and $R^9$, $R^9$ and $R^{10}$, $R^{10}$ and $R^{11}$, $R^{11}$ and $R^{12}$, $R^{12}$ and $R^{13}$, as well as $R^{13}$ and $R^{14}$ may combine to form a ring group; $Z^1$-$Z^5$ represent hydrogen or independently selected substituents, provided that $Z^1$ and $Z^2$, $Z^2$ and $Z^3$, $Z^3$ and $Z^4$, as well as $Z^4$ and $Z^5$ may combine to form a ring group.

Examples of phosphorescent emitters having tetradentate C,N-cyclometallating ligands include (PD-16) through (PD-18) represented below.

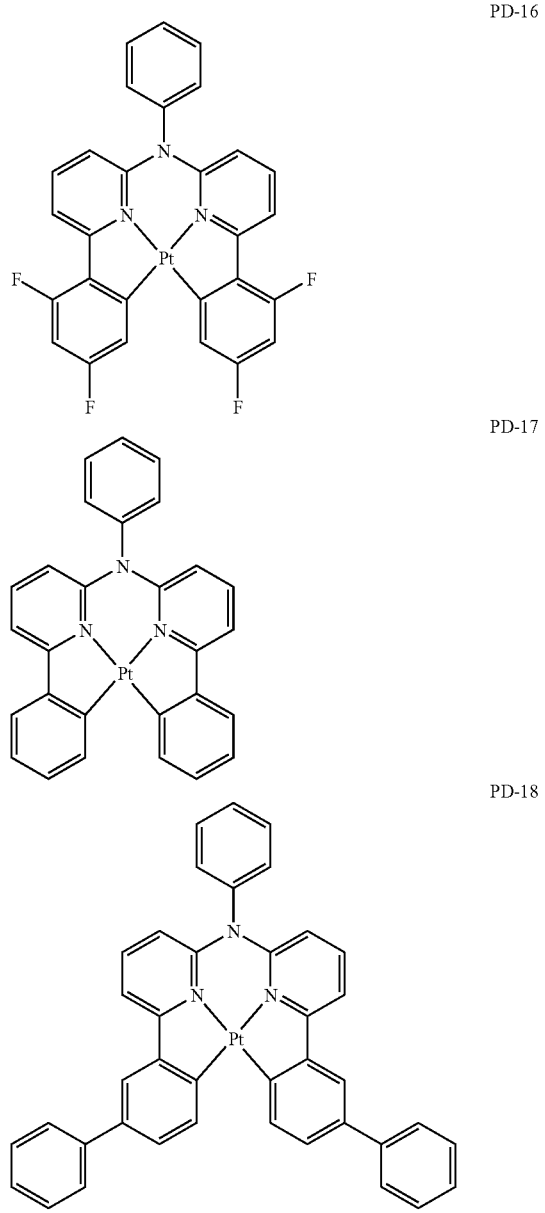

PD-16

PD-17

PD-18

The emission wavelengths (color) of C,N-cyclometallated phosphorescent materials according to Formula (PDF-1) through (PDF-4) are governed principally by the lowest energy optical transition of the complex and hence by the choice of the C,N-cyclometallating ligand. For example, 2-phenyl-pyridinato-N,$C^{2'}$ complexes are typically green emissive while 1-phenyl-isoquinolinolato-N,$C^{2'}$ complexes are typically red emissive. In the case of complexes having more than one C,N-cyclometallating ligand, the emission will be that of the ligand having the property of longest wavelength emission. Emission wavelengths may be further shifted by the effects of substituent groups on the C,N-cyclometallating ligands. For example, substitution of electron donating groups at appropriate positions on ring A, or electron withdrawing groups on ring B tend to blue-shift the emission relative to the unsubstituted C,N-cyclometallated ligand complex. Selecting a monoanionic bidentate ligand X,Y in Formula (PDF-1) having more electron withdrawing properties also tends to blue-shift the emission of a C,N-cyclometallated ligand complex. Examples of complexes having both monoanionic bidentate ligands possessing electron-withdrawing properties on ring A, and electron-withdrawing substituent groups on ring B include bis(2-(4',6'-difluorophenyl)-pyridinato-N,$C^{2'}$)iridium(III)(picolinate); bis(2-(5'-(4"-trifluoromethylphenyl)-4',6'-difluorophenyl)-pyridinato-N,$C^{2'}$)iridium(III)(picolinate); bis(2-(5'-phenyl-4',6'-difluorophenyl)-pyridinato-N,$C^{2'}$)iridium(III)(picolinate); bis(2-(5'-cyano-4',6'-difluorophenyl)-pyridinato-N, $C^{2'}$)iridium(III)(picolinate); bis(2-(4',6'-difluorophenyl)-pyridinato-N,$C^{2'}$)iridium(III)(tetrakis(1-pyrazolyl)borate); bis(2-(4',6'-difluorophenyl)-pyridinato-N,$C^{2'}$)(2-((3-trifluoromethyl)-1H-pyrazol-5-yl)-pyridinato-N,N')iridium(III); bis(2-(4',6'-difluorophenyl)-4-methylpyridinato-N,$C^{2'}$)(2-((3-trifluoromethyl)-1H-pyrazol-5-yl)-pyridinato-N,N')iridium(III); and bis(2-(4',6'-difluorophenyl)-4-methoxypyridinato-N,$C^{2'}$)(2-((3-trifluoromethyl)-1H-pyrazol-5-yl) pyridinato-N,N')iridium(III).

The central metal atom in phosphorescent materials according to Formula (PDF-1) may be Rh, Ir, Pd, or Pt. Preferred metal atoms are Ir and Pt since these tend to give higher phosphorescent quantum efficiencies according to the stronger spin-orbit coupling interactions generally obtained with elements in the third transition series.

Other phosphorescent materials that do not involve C,N-cyclometallating ligands are known. Phosphorescent complexes of Pt(II), Ir(I), and Rh(I) with maleonitriledithiolate have been reported (C. E. Johnson et al, J. Am. Chem. Soc., 105, 1795-1802 (1983)). Re(I) tricarbonyl diimine complexes are also known to be highly phosphorescent (M. Wrighton and D. L. Morse, J. Am. Chem. Soc., 96, 998-1003 (1974); D. J. Stufkens, Comments Inorg. Chem., 13, 359-385 (1992); V. W. W. Yam, Chem. Commun., 2001, 789-796)). Os(II) complexes containing a combination of ligands including cyano ligands and bipyridyl or phenanthroline ligands have also been demonstrated in a polymer OLED (Y. Ma et al, Synthetic Metals, 94, 245-248 (1998)).

Porphyrin complexes such as 2,3,7,8,12,13,17,18-octaethyl-21H,23H-porphine platinum(II) are also useful phosphorescent materials.

Still other examples of useful phosphorescent materials include coordination complexes of the trivalent lanthanides such as $Tb^{3+}$ and $Eu^{3+}$ (J. Kido et al., Chem Lett., 657 (1990); J Alloys and Compounds, 192, 30-33 (1993); Jpn J Appl Phys, 35, L394-6 (1996) and Appl. Phys. Lett., 65, 2124 (1994)).

Additional information on suitable phosphorescent materials, incorporated herein by reference, can be found in U.S. Pat. No. 6,303,238, WO00/57676, WO00/70655, WO01/41512, US2002/0182441, US2003/0017361, US2003/0072964, U.S. Pat. No. 6,413,656, U.S. Pat. No. 6,687,266, US2004/0086743, US2004/0121184, US2003/0059646, US2003/0054198, EP1239526, EP1238981, EP1244155, US2002/0100906, US2003/0068526, US2003/0068535, JP2003073387, JP2003/073388, U.S. Pat. No. 6,677,060, US2003/0235712, US2004/0013905, U.S. Pat. No. 6,733, 905, U.S. Pat. No. 6,780,528, US2003/0040627, JP2003059667, JP2003073665, US2002/0121638, EP1371708, US2003/010877, WO03/040256, US2003/ 0096138, US2003/0173896, U.S. Pat. No. 6,670,645, US2004/0068132, WO2004/015025, US2004/0072018, US2002/0134984, WO03/079737, WO2004/020448, WO03/ 091355, U.S. Ser. No. 10/729,402, U.S. Ser. No. 10/729,712, U.S. Ser. No. 10/729,738, U.S. Ser. No. 10/729,238, U.S. Ser. No. 10/729,246, U.S. Ser. No. 10/729,207, and U.S. Ser. No. 10/729,263.

Blocking Layers

In addition to suitable hosts and transporting materials, an OLED device employing a phosphorescent material often requires at least one exciton or hole blocking layer to help confine the excitons or electron-hole recombination events to the light emitting layer comprising the host and phosphorescent material. In one embodiment, such a blocking layer 110 would be placed between the electron transporting layer and the light emitting layer—see FIG. 1. In this case, the ionization potential of the blocking layer should be such that there is an energy barrier for hole migration from the light emitting layer into the electron-transporting layer, while the electron affinity should be such that electrons pass readily from the electron transporting layer into the light emitting layer. It is further desired, but not absolutely required, that the triplet energy of the blocking material be greater than that of the phosphorescent material. Suitable hole blocking materials are described in US 20020015859, WO 00/70655 and WO 01/93642. Two examples of useful materials are bathocuproine (BCP) and bis(2-methyl-8-quinolinolato)(4-phenylphenolato)Aluminum(III) (BAlQ or 1). Metal complexes other than BAlQ are also known to block holes and excitons as described in US 20030068528. US 20030175553 describes the use of fac-tris(1-phenylpyrazolato-N,$C_2$)iridium(III) (Irppz) in an electron/exciton blocking layer.

Electron Transporting Layer (ETL)

The electron transporting material deposited in said electron transporting layer between the cathode and the light emitting layer may be the same or different from an electron transporting co-host material. The electron transporting layer may include more than one electron transporting compound, deposited as a blend or divided into separate layers.

Preferred thin film-forming materials for use in constructing the electron transporting layer of the organic EL devices are metal-chelated oxinoid compounds, including chelates of oxine itself (also commonly referred to as 8-quinolinol or 8-hydroxyquinoline). Such compounds help to inject and transport electrons, exhibiting high levels of performance, and are readily fabricated in the form of thin films. Exemplary of contemplated oxinoid compounds are those satisfying structural formula (ET1) below:

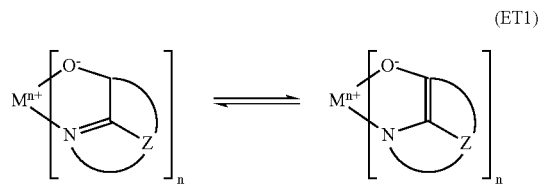

(ET1)

wherein
M represents a metal;
n is an integer of from 1 to 4; and
Z independently in each occurrence represents the atoms completing a nucleus having at least two fused aromatic rings.

From the foregoing it is apparent that the metal can be a monovalent, divalent, trivalent, or tetravalent metal. The metal can, for example, be an alkali metal, such as lithium, sodium, or potassium; an alkaline earth metal, such as beryllium, magnesium, or calcium; an earth metal, such aluminum or gallium, or a transition metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less. Illustrative of useful chelated oxinoid compounds are the following:

CO-1: Aluminum trisoxine [alias, tris(8-quinolinolato)aluminum(III); Alq];
CO-2: Magnesium bisoxine[alias, bis(8-quinolinolato)magnesium(II)];
CO-3: Bis[benzo{f}-8-quinolinolato]zinc (II);
CO-4: Bis(2-methyl-8-quinolinolato)aluminum(III)-μ-oxo-bis(2-methyl-8-quinolinolato) aluminum(III);
CO-5: Indium trisoxine [alias, tris(8-quinolinolato)indium];
CO-6: Aluminum tris(5-methyloxine) [alias, tris(5-methyl-8-quinolinolato) aluminum(III)];
CO-7: Lithium oxine [alias, (8-quinolinolato)lithium(I)];
CO-8: Gallium oxine [alias, tris(8-quinolinolato)gallium (III)];
CO-9: Zirconium oxine [alias, tetra(8-quinolinolato)zirconium(IV)].

Other electron transporting materials suitable for use in the electron transporting layer include various butadiene derivatives as disclosed in U.S. Pat. No. 4,356,429 and various heterocyclic optical brighteners as described in U.S. Pat. No. 4,539,507. Benzazoles satisfying structural formula (ET2) are also useful electron transporting materials:

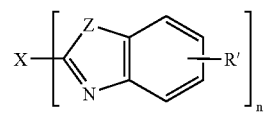

(ET2)

wherein
n is an integer of 3 to 8;
Z is O, NR or S; and
R and R' are individually hydrogen; alkyl of from 1 to 24 carbon atoms, for example, propyl, t-butyl, heptyl, and the like; aryl or hetero-atom substituted aryl of from 5 to 20 carbon atoms for example phenyl and naphthyl, furyl, thienyl, pyridyl, quinolinyl and other heterocyclic systems; or halo such as chloro, fluoro; or atoms necessary to complete a fused aromatic ring; and
X is a linkage unit consisting of carbon, alkyl, aryl, substituted alkyl, or substituted aryl, which conjugately or unconjugately connects the multiple benzazoles together. An example of a useful benzazole is 2,2',2"-(1,3,5-phenylene)tris [1-phenyl-1H-benzimidazole] (TPBI) disclosed in Shi et al. in U.S. Pat. No. 5,766,779.

Other electron transporting materials suitable for use in the electron transporting layer may be selected from triazines, triazoles, imidazoles, oxazoles, thiazoles and their derivatives, polybenzobisazoles, pyridine- and quinoline-based materials, cyano-containing materials, perfluorinated materials, and anthracenes.

The electron transporting layer or a portion of the electron transporting layer adjacent the cathode may further be doped with an alkali metal to reduce electron injection barriers and hence lower the drive voltage of the device. Suitable alkali metals for this purpose include lithium and cesium.

Cathode

When light emission is viewed solely through the anode 103, the cathode can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising a thin electron injecting layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such bilayer cathode is comprised of a thin layer of LiF followed by a thicker layer of Al as described in U.S. Pat. No. 5,677,572. An ETL material doped with an alkali metal, for example, Li-doped Alq, as disclosed in U.S. Pat. No. 6,013,384, is another example of a useful EIL. Other useful cathode material sets include, but are not limited to, those disclosed in U.S. Pat. No. 5,059,861, U.S. Pat. No. 5,059,862, and U.S. Pat. No. 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. No. 4,885,211, U.S. Pat. No. 5,247,190, JP3234963, U.S. Pat. No. 5,703,436, U.S. Pat. No. 5,608,287, U.S. Pat. No. 5,837,391, U.S. Pat. No. 5,677,572, U.S. Pat. No. 5,776,622, U.S. Pat. No. 5,776,623, U.S. Pat. No. 5,714,838, U.S. Pat. No. 5,969,474, U.S. Pat. No. 5,739,545, U.S. Pat. No. 5,981,306, U.S. Pat. No. 6,137,223, U.S. Pat. No. 6,140,763, U.S. Pat. No. 6,172,459, EP1076368, U.S. Pat. No. 6,278,236, and U.S. Pat. No. 6,284,393. Cathode materials are typically deposited by any suitable methods such as evaporation, sputtering, or chemical vapor deposition. When needed, patterning can be achieved through many well known methods including, but not limited to, through-mask deposition, integral shadow masking as described in U.S. Pat. No. 5,276,380 and EP0732868, laser ablation, and selective chemical vapor deposition.

Other Common Organic Layers and Device Architecture

In some instances, layers 109 and 111 can optionally be collapsed into a single layer that serves the function of supporting both light emission and electron transportation. It also known in the art that emitting dopants may be added to the hole transporting layer, which may serve as a host. Multiple dopants may be added to one or more layers in order to create a white-emitting OLED, for example, by combining blue- and yellow-emitting materials, cyan- and red-emitting materials, or red-, green-, and blue-emitting materials. White-emitting devices are described, for example, in EP1187235, EP1182244, U.S. Pat. No. 5,683,823, U.S. Pat. No. 5,503,910, U.S. Pat. No. 5,405,709, and U.S. Pat. No. 5,283,182, US20020186214, US20020025419, US20040009367, and U.S. Pat. No. 6,627,333.

A stacked device architecture is another example, as taught in U.S. Pat. No. 5,703,436 and U.S. Pat. No. 6,337,492.

Deposition of Organic Layers

The organic materials mentioned above are suitably deposited through a vapor-phase method such as sublimation, but can be deposited from a fluid, for example, from a solvent with an optional binder to improve film formation. If the material is a polymer, solvent deposition is useful but other methods can be used, such as sputtering or thermal transfer from a donor sheet. The material to be deposited by sublimation can be vaporized from a sublimation "boat" often comprised of a quartz or tantalum material, e.g., as described in U.S. Pat. No. 6,237,529, or can be first coated onto a donor sheet and then sublimed in closer proximity to the substrate. Layers with a mixture of materials can utilize separate sublimation boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. No. 5,688,551, U.S. Pat. No. 5,851,709 and U.S. Pat. No. 6,066,357) and an inkjet method (U.S. Pat. No. 6,066,357).

One preferred method for depositing materials is described in US 2004/0255857 and U.S. Ser. No. 10/945,941 where different source evaporators are used to evaporate each of the materials. A second preferred method involves the use of flash evaporation where materials are metered along a material feed path in which the material feed path is temperature controlled. Such a preferred method is described in the following co-assigned patent applications: U.S. Ser. No. 10/784,585; U.S. Ser. No. 10/805,980; U.S. Ser. No. 10/945,940; U.S. Ser. No. 10/945,941; U.S. Ser. No. 11/050,924; and U.S. Ser. No. 11/050,934. Using this second method, each material may be evaporated using different source evaporators or the solid materials may be mixed prior to evaporation using the same source evaporator.

Encapsulation

Most OLED devices are sensitive to moisture or oxygen, or both, so they are commonly sealed in an inert atmosphere such as nitrogen or argon. In sealing an OLED device in an inert environment, a protective cover can be attached using an organic adhesive, a metal solder, or a low melting temperature glass. Commonly, a getter or desiccant is also provided within the sealed space. Useful getters and desiccants include, alkali and alkaline metals, alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiOx, Teflon, and alternating inorganic/polymeric layers are known in the art for encapsulation.

Optical Optimization

OLED devices can employ various well-known optical effects in order to enhance its properties if desired. This includes optimizing layer thicknesses to yield maximum light transmission, providing dielectric mirror structures, replacing reflective electrodes with light-absorbing electrodes, providing anti glare or anti-reflection coatings over the display, providing a polarizing medium over the display, or providing colored, neutral density, or color conversion filters in functional relationship with the light emitting areas of the display. Filters, polarizers, and anti-glare or anti-reflection coatings can also be provided over a cover or as part of a cover.

The OLED device may have a microcavity structure. In one useful example, one of the metallic electrodes is essentially opaque and reflective; the other one is reflective and semi-transparent. The reflective electrode is preferably selected from Au, Ag, Mg, Ca, Al, or alloys thereof. Because of the presence of the two reflecting metal electrodes, the device has a microcavity structure. The strong optical interference in this structure results in a resonance condition. Emission near the resonance wavelength is enhanced and emission away from the resonance wavelength is depressed. The optical path length can be tuned by selecting the thickness of the organic layers or by placing a transparent optical spacer between the electrodes. For example, an OLED device can have an ITO spacer layer placed between a reflective anode and the organic EL media, with a semitransparent cathode over the organic EL media.

The entire contents of the patents and other publications referred to in this specification are incorporated herein by reference.

EXAMPLES

Preparation of 2H-1-Benzopyran-2-one, 3-(2-pyridinyl (3-(2-pydinyl)coumarin or pcm): o-hydoxycarbonylbenzene (40 mmol) and 2-pyridylacetonitrile (40 mmol) were added to an aqueous solution of NaOH (0.05 N, 200 ml). The mixture was vigorously stirred at 90° C. for 3.5 hours. After cooling the solid was filtered, washed with cold water and dried. The crude compound was purified by crystallization from ethanol. yield: 92%. MS: m/z calcd 223. found 224 [M+1].

Synthesis of Ir(3-pyridylcoumarin)$_2$(acac) (Ir(pcm)$_2$acac) (CMPD-1): Cyclometalated Ir(III) μ-chloro-bridged dimer of (pcm)$_2$Ir (μ-Cl)$_2$Ir(pcm)$_2$ was synthesized according to the Nonoyama route, by refluxing IrCl$_3$.nH$_2$O with 2-2.5 equiv of 3-pyridylcoumarin in a 3:1 mixture of 2-ethoxyethanol and water. The chloro-bridged dimer complex (0.08 mmol), 0.2 mmol of acetyl acetone, and 85-90 mg of sodium carbonate were heated to reflux in dichloroethane under an inert atmosphere for 12-15 hours. After cooling, the mixture was extracted with water, dried with MgSO$_4$, and concentrated. The crude product was purified by flash chromatography on a silica gel column with dichloromethane to yield 85% of the pure Ir(pcm)$_2$acac. MS: m/z calcd 736. found 737 [M+1].

Synthesis of mer-Ir(pcm)$_3$ (INV-3): (pcm)$_2$Ir(μ-Cl)$_2$Ir (pcm)$_2$ (3 mmol), 2.5 equiv of the ligand, and 5-10 equiv of sodium carbonate were heated to reflux in 2-ethoxyethanol under an inert atmosphere overnight. After the mixture was cooled to room temperature, distilled water was added; the resulting precipitate was filtered, washed with two more portions of distilled water, and air-dried. The crude product was purified by flash chromatography on a silica gel column with dichloromethane, and recrystallized from a dichloromethane/methol mixture to yield 72% of the pure mer-Ir(pcm)$_3$. MS: m/z calcd 859. found 860 [M+1].

Synthesis of mer-Ir(2-phenylpyridyl)$_2$(3-pyridylcoumarin) (mer-Ir(ppy)$_2$ pcm): (ppy)$_2$Ir(μ-Cl)$_2$Ir(ppy)$_2$ (2 mmol), 2.5 equiv of the ligand, and 5-10 equiv of sodium carbonate were heated to reflux in 2-ethoxyethanol under an inert atmosphere overnight. After the mixture was cooled to room temperature, distilled water was added; the resulting precipitate was filtered, washed with two more portions of distilled water, and air-dried. The crude product was purified by flash chromatography on a silica gel column with dichloromethane, and recrystallized from a dichloromethane/methanol mixture to yield 72% of the pure mer-Ir(ppy)$_2$ pcm. MS: m/z calcd 722. found 723 [M+1].

Isomerization of meridional iridium complex mer-Ir(ppy)$_2$(pcm) in sealed system: A sample of mer-Ir(1-piq)$_2$(ppy) (5 g, mer/fac ratio>99:1) was placed in a small ampoule. The ampoule was sealed under high vacuum and placed in an oven. The temperature of the oven was set to 320° C. After 16 hour, the ampoule was taken out and cooled to room temperature, the mer/fac ratio of the sample was determined by HPLC to be 14:66 (measured by area). In addition, a new compound with a slightly shorter retention time (12% by area) was formed. Product separation was achieved through purification by flash chromatography on a silica gel column with 5% methanol in dichloromethane. fac-Ir(ppy)$_2$(pcm) (INV-2) (2.5 g) MS: m/z calcd 722. found 723 [M+1]. fac-Ir(pcm)$_2$ (ppy) (INV-1) (0.6 g) MS: m/z calcd 791. found 792 [M+1].

Examples 1-1 Through 1-6

EL devices (Examples 1-1 through 1-6) satisfying the requirements of the invention were constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon (CF$_x$) hole injecting layer (HIL) was deposited by plasma-assisted deposition of CHF$_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 75 nm for Examples 1-1 through 1-4 and 95 nm for Examples 1-5 and 1-6.
4. A 40 nm light emitting layer (LEL) consisting of a mixture of CBP, and INV-1 as a phosphorescent emitter was then vacuum deposited onto the hole transporting layer. The weight % of the phosphorescent emitter is shown in Table 1.
5. A hole blocking layer of BAlq having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 1-1 had the following structure of layers: ITO|CF$_x$ (1 nm)|NPB (75 nm)|CBP+4 wt. % INV-1 (40 nm)|BAlq (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm$^2$ and the results are reported in Table 1 in the form of luminous yield (cd/A), voltage (V), power efficiency (1 m/W), and CIE (Commission Internationale de l'Eclairage) coordinates. The devices were also tested for operational lifetime. They were operated at 20 mA/cm$^2$ at room temperature with an AC Drive at 100 Hz with a −14 V reverse bias. The lifetime to T$_{60}$ is shown in Table 1 as the number of hours the device operated before the light output dropped to 60% of its initial light output.

TABLE 1

Evaluation results for Devices 1-1 through 1-6.

| Device | Phosphorescent emitter Wt. % | Voltage, V | Luminous Yield, cd/A | Power efficiency, lm/W | CIEx; CIEy | Lifetime, $T_{60}$, hours |
|---|---|---|---|---|---|---|
| 1-1 | 4 | 6.59 | 11.4 | 5.45 | 0.4121 0.5477 | 402 |
| 1-2 | 6 | 6.38 | 10.9 | 5.37 | 0.4125 0.5467 | 431 |
| 1-3 | 8 | 6.19 | 9.72 | 4.93 | 0.4106 0.5455 | 414 |
| 1-4 | 10 | 6.02 | 8.69 | 4.54 | 0.4072 0.5434 | 418 |
| 1-5 | 6 | 6.38 | 12.1 | 5.95 | 0.4130 0.5508 | 365 |
| 1-6 | 8 | 6.16 | 10.8 | 5.48 | 0.4118 0.5491 | 480 |

Examples 2-1 Through 2-2

EL devices (Example 2-1 and 2-2) satisfying the requirements of the invention were constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon ($CF_x$) hole injecting layer (HIL) was deposited by plasma-assisted deposition of $CHF_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 95 nm.
4. A exciton blocking layer (EBL) of TCTA was vacuum deposited over the HTL to a thickness of 10 nm.
5. A 35 nm light emitting layer (LEL) consisting of a mixture of TPBI, TCTA, and INV-1 as a phosphorescent emitter was then vacuum deposited onto the exciton blocking layer. The layer consisted of 30% TCTA by weight, the amount of the phosphorescent emitter is shown in Table 2, and the remainder of the layer was TPBI.
5. A hole blocking layer of TPBI having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 2-1 had the following structure of layers: ITO|$CF_x$ (1 nm)|NPB (95 nm)|TCTA (10 nm)|TCTA (30%)+TPBI (62%)+INV-1 (8%) (35 nm)|TPBI (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm² and the results are reported in Table 2 in the form of luminous yield (cd/A), voltage (V), power efficiency (1 m/W), and CIE (Commission Internationale de l'Eclairage) coordinates.

TABLE 2

Evaluation results for Devices 2-1 through 2-2.

| Device | Phosphorescent emitter Wt. % | Voltage, V | Luminous Yield, cd/A | Power efficiency, lm/W | CIEx; CIEy |
|---|---|---|---|---|---|
| 2-1 | 8 | 4.49 | 74.1 | 51.8 | 0.3960 0.5864 |
| 2-2 | 10 | 6.38 | 72.9 | 52.5 | 0.3985 0.5839 |

Examples 3-1 Through 3-6

EL devices (Example 3-1 and 3-6) satisfying the requirements of the invention were constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon ($CF_x$) hole injecting layer (HIL) was deposited by plasma-assisted deposition of $CHF_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 75 nm for Examples 3-1 through 3-4 and 95 nm for Examples 3-5 and 3-6.
4. A 40 nm light emitting layer (LEL) consisting of a mixture of CBP, and INV-2 as a phosphorescent emitter was then vacuum deposited onto the hole transporting layer. The weight % of the phosphorescent emitter is shown in Table 3.
5. A hole blocking layer of BAlq having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 3-1 had the following structure of layers: ITO|$CF_x$ (1 nm)|NPB (75 nm)|CBP+4 wt. % INV-2 (40 nm)|BAlq (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm² and the results are reported in Table 3 in the form of luminous yield (cd/A), voltage (V), power efficiency (1 m/W), and CIE (Commission Internationale de l'Eclairage) coordinates. The devices were also tested for operational lifetime. They were operated at 20 mA/cm² at room temperature with an AC Drive at 100 Hz with a −14 V reverse bias. The lifetime to $T_{50}$ is shown in Table 3 as the number of hours the device operated before the light output dropped to 50% of its initial light output.

TABLE 3

Evaluation results for Devices 3-1 through 3-6.

| Device | Phosphorescent emitter Wt. % | Voltage, V | Luminous Yield, cd/A | Power efficiency, lm/W | CIEx; CIEy | Lifetime, $T_{50}$, hours |
|---|---|---|---|---|---|---|
| 3-1 | 4 | 6.98 | 12.9 | 5.79 | 0.4107 0.5503 | 170 |
| 3-2 | 6 | 6.85 | 10.0 | 4.59 | 0.4069 0.5474 | 267 |
| 3-3 | 8 | 6.55 | 9.60 | 4.60 | 0.4070 0.5487 | 314 |
| 3-4 | 10 | 6.42 | 8.25 | 4.03 | 0.4032 0.5473 | 294 |
| 3-5 | 6 | 6.81 | 6.59 | 3.04 | 0.3890 0.5469 | >360 |
| 3-6 | 8 | 6.33 | 8.21 | 4.07 | 0.4040 0.5500 | 345 |

Examples 4-1 Through 4-2

EL devices (Example 4-1 and 4-2) satisfying the requirements of the invention were constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon ($CF_x$) hole injecting layer (HIL) was deposited by plasma-assisted deposition of $CHF_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 95 nm.
4. A exciton blocking layer (EBL) of TCTA was vacuum deposited over the HTL to a thickness of 10 nm.
5. A 35 nm light emitting layer (LEL) consisting of a mixture of TPBI, TCTA, and INV-2 as a phosphorescent emitter was then vacuum deposited onto the exciton blocking layer. The layer consisted of 30% TCTA by weight, the amount of the phosphorescent emitter is shown in Table 4, and the remainder of the layer was TPBI.
5. A hole blocking layer of TPBI having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 4-1 had the following structure of layers: ITO|$CF_x$ (1 nm)|NPB (95 nm)|TCTA (10 nm)|TCTA (30%)+TPBI (62%)+INV-2 (8%) (35 nm)|TPBI (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm² and the results are reported in Table 4 in the form of luminous yield (cd/A), voltage (V), power efficiency (1 m/W), and CIE (Commission Internationale de l'Eclairage) coordinates.

TABLE 4

Evaluation results for Devices 4-1 through 4-2.

| Device | Phosphorescent emitter Wt. % | Voltage, V | Luminous Yield, cd/A | Power efficiency, lm/W | CIEx; CIEy |
|---|---|---|---|---|---|
| 4-1 | 8 | 4.42 | 68.3 | 48.5 | 0.4428 0.5480 |
| 4-2 | 10 | 4.37 | 67.7 | 48.7 | 0.4448 0.5466 |

Examples 5-1 Through 5-5

EL devices (Examples 5-1 through 5-5) satisfying the requirements of the invention were constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon ($CF_x$) hole injecting layer (HIL) was deposited by plasma-assisted deposition of $CHF_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 75 nm for Examples 5-1 through 5-4 and 95 nm for Examples 5-5.
4. A 40 nm light emitting layer (LEL) consisting of a mixture of CBP, and INV-3 as a phosphorescent emitter was then vacuum deposited onto the hole transporting layer. The weight % of the phosphorescent emitter is shown in Table 5.
5. A hole blocking layer of BAlq having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 5-1 had the following structure of layers: ITO|$CF_x$ (1 nm)|NPB (75 nm)|CBP+4 wt. % INV-3 (40 nm)|BAlq (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm² and the results are reported in Table 5 in the form of luminous yield (cd/A), voltage (V), power efficiency (1 m/W), and CIE (Commission Internationale de l'Eclairage) coordinates. The devices were also tested for operational lifetime. They were operated at 20 mA/cm² at room temperature with an AC Drive at 100 Hz with a −14 V reverse bias. The lifetime to $T_{50}$ is shown in Table 5 as the number of hours the device operated before the light output dropped to 50% of its initial light output.

TABLE 5

Evaluation results for Devices 5-1 through 5-5.

| Device | Phosphorescent emitter Wt. % | Voltage, V | Luminous Yield, cd/A | Power efficiency, lm/W | CIEx; CIEy | Lifetime, $T_{50}$, hours |
|---|---|---|---|---|---|---|
| 5-1 | 4 | 7.51 | 10.1 | 4.23 | 0.3934 0.5639 | 46 |
| 5-2 | 6 | 7.38 | 11.5 | 4.88 | 0.3997 0.5619 | 32 |
| 5-3 | 8 | 7.25 | 11.5 | 4.98 | 0.4057 0.5587 | 35 |
| 5-4 | 10 | 7.23 | 10.5 | 4.55 | 0.4093 0.5559 | 36 |
| 5-5 | 6 | 7.05 | 7.70 | 3.43 | 0.4015 0.5652 | N/A |

Examples 6-1 Through 6-2

EL devices (Example 6-1 and 6-2) satisfying the requirements of the invention were constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon ($CF_x$) hole injecting layer (HIL) was deposited by plasma-assisted deposition of $CHF_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 95 nm.
4. An exciton blocking layer (EBL) of TCTA was vacuum deposited over the HTL to a thickness of 10 nm.
5. A 35 nm light emitting layer (LEL) consisting of a mixture of TPBI, TCTA, and INV-3 as a phosphorescent emitter was then vacuum deposited onto the exciton blocking layer. The layer consisted of 30% TCTA by weight, the amount of the phosphorescent emitter is shown in Table 6, and the remainder of the layer was TPBI.
5. A hole blocking layer of TPBI having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 6-1 had the following structure of layers: ITO|$CF_x$ (1 nm)|NPB (95 nm)|TCTA (10 nm)|TCTA (30%)+TPBI (62%)+INV-3 (8%) (35 nm)|TPBI (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm² and the results are reported in Table 6 in the form of luminous yield (cd/A), voltage (V), power efficiency (1 m/W), and CIE (Commission Internationale de l'Eclairage) coordinates.

TABLE 6

Evaluation results for Devices 6-1 through 6-2.

| Device | Phosphorescent emitter Wt. % | Voltage, V | Luminous Yield, cd/A | Power efficiency, lm/W | CIEx; CIEy |
|---|---|---|---|---|---|
| 6-1 | 8 | 5.01 | 39.0 | 24.4 | 0.4239 0.5625 |
| 6-2 | 10 | 5.12 | 39.2 | 24.0 | 0.4272 0.5601 |

Example 7-1

An EL device (Example 7-1) not satisfying the requirements of the invention was constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon ($CF_x$) hole injecting layer (HIL) was deposited by plasma-assisted deposition of $CHF_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 95 nm for Examples 7-1.
4. A 35 nm light emitting layer (LEL) consisting of a mixture of CBP, and 6 weight % of Ir(ppy)$_3$ as a phosphorescent emitter was then vacuum deposited onto the hole transporting layer.
5. A hole blocking layer of BAlq having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 7-1 had the following structure of layers: ITO|$CF_x$ (1 nm)|NPB (95 nm)|CBP+6 wt. % Ir(ppy)$_3$ (35 nm)|BAlq (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm² and the results are reported in Table 7 in the form of luminous yield (cd/A), voltage (V), power efficiency (1 m/W), and CIE (Commission Internationale de l'Eclairage) coordinates. The devices were also tested for operational lifetime. They were operated at 20 mA/cm² at room temperature with an AC Drive at 100 Hz with a −14 V reverse bias. The lifetime to $T_{50}$ is shown in Table 7 as the number of hours the device operated before the light output dropped to 50% of its initial light output.

TABLE 7

Evaluation results for Device 7-1.

| Device | Phosphorescent emitter Wt. % | Voltage, V | Luminous Yield, cd/A | Power efficiency, lm/W | CIEx; CIEy | Lifetime, $T_{50}$, hours |
|---|---|---|---|---|---|---|
| 7-1 | 6 | 6.10 | 34.2 | 17.6 | 0.3018 0.6255 | 173 |

Example 8-1

An EL device (Example 8-1) not satisfying the requirements of the invention was constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon ($CF_x$) hole injecting layer (HIL) was deposited by plasma-assisted deposition of $CHF_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 95 nm.
4. An exciton blocking layer (EBL) of TCTA was vacuum deposited over the HTL to a thickness of 10 nm.
5. A 35 nm light emitting layer (LEL) consisting of a mixture of TPBI, TCTA, and $Ir(ppy)_3$ as a phosphorescent emitter was then vacuum deposited onto the exciton blocking layer. The layer consisted of 30% TCTA by weight, 6 weight % of $Ir(ppy)_3$, and the remainder of the layer was TPBI.
5. A hole blocking layer of TPBI having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 8-1 had the following structure of layers: ITO|$CF_x$ (1 nm)|NPB (95 nm)|TCTA (10 nm)|TCTA (30%)+TPBI (62%)+$Ir(ppy)_3$ (6%) (35 nm)|TPBI (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm² and the results are reported in Table 8 in the form of luminous yield (cd/A), voltage (V), power efficiency (1 m/W), and CIE (Commission Internationale de l'Eclairage) coordinates.

TABLE 8

Evaluation results for Device 8-1.

| Device | Phosphorescent emitter Wt. % | Voltage, V | Luminous Yield, cd/A | Power efficiency, lm/W | CIEx; CIEy |
|---|---|---|---|---|---|
| 6-1 | 6 | 5.15 | 66.3 | 40.5 | 0.3115 0.6257 |

Comparison Example 9-1

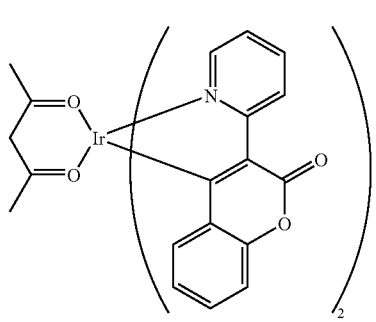

CMPD-1

An EL device (Example 9-1) not satisfying the requirements of the invention was constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon ($CF_x$) hole injecting layer (HIL) was deposited by plasma-assisted deposition of $CHF_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 40 nm.
4. A 40 nm light emitting layer (LEL) consisting of a mixture of CBP, and 8 weight % of CMPD-1 as a phosphorescent emitter was then vacuum deposited onto the hole transporting layer.
5. A hole blocking layer of BAlq having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 9-1 had the following structure of layers: ITO|$CF_x$ (1 nm)|NPB (40 nm)|CBP+8 wt. % CMPD-1 (40 nm)|BAlq (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm² and the results are reported in Table 9 in the form of luminous yield (cd/A), voltage (V), power efficiency (1 m/W), and CIE (Commission Internationale de l'Eclairage) coordinates. The devices were also tested for operational lifetime. They were operated at 20 mA/cm² at room temperature with an AC Drive at 100 Hz with a −14 V reverse bias. The lifetime to $T_{50}$ is shown in Table 9 as the number of hours the device operated before the light output dropped to 50% of its initial light output.

TABLE 9

Evaluation results for Comparison Device 9-1.

| Device | Phosphorescent emitter Wt. % | Voltage, V | Luminous Yield, cd/A | Power efficiency, lm/W | CIEx; CIEy | Lifetime, $T_{50}$, hours |
|---|---|---|---|---|---|---|
| 9-1 | 8 | 6.98 | 27.1 | 5.08 | 0.3951 0.5836 | 22 |

Comparison Example 9-1 shows that an organometallic coumarin compound with organometallic ligands is advantaged over an organometallic coumarin compound with a non-organometallic ligand. In particular the voltage, luminous yield, power efficiency, lifetime; or all of the above are improved.

Comparison Example 10

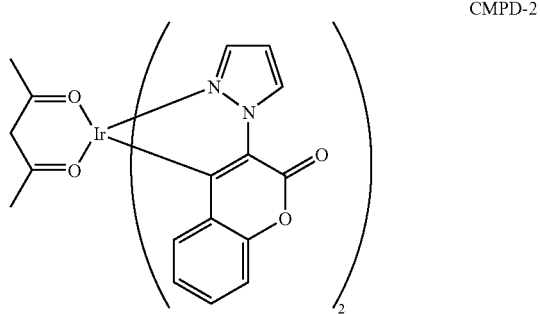

CMPD-2

A second example of a phosphorescent iridium material containing a coumarin and also a non-cyclometallated ligand is shown as CMPD-2. The measured quantum yield (QY) is low, at 0.25. When a phosphorescent material has a low quantum yield it is not expected to perform well as a dopant in a OLED device.

Preparation of 6H-[2]benzopyrano[4,3-b]pyridin-6-one: To a suspension of 3-methoxy-2-(1H)-pyridone (10 mmol) in 10 mol of acetone was added $K_2CO_3$ (20 mmol) and TBAB (1.0 mmol). After stirring at room temperature for 30 min, 2-bromobenzoyl chloride (10 mmol) was added carefully. The mixture was stirred overnight. To the concentrated reaction mixture was added water and the mixture was extracted with $CH_2Cl_2$. The organic layer was washed with aqueous $NH_4Cl$, dried over $MgSO_4$, and concentrated under vacuum. The crude product was purified by flash column chromatography with hexane/ethylacetate (80/20) to give O-acylation product. To a refluxing solution of bromide made above (1 equiv.) was added $(CH_3Si)_3SiH$ (1.5 equiv.) and AIBN (0.05 equiv.). After 2 hours, a second portion of AIBN (0.05 equiv.) was added and the reaction mixture was refluxed for an additional 4-10 hours. The concentrated reaction mixture was triturated with BuCl or further purified by flash chromatography to give the cyclization product (azabenzoisocoumarin or abic). MS: m/z calcd 196. found 197 [M+1].

Synthesis of fac-Ir(azabenzoisocoumarin)$_2$(ppy) (fac-Ir (abic)$_2$ppy) (INV-21): Cyclometalated Ir(III) µ-chloro-bridged dimer of (abic)$_2$Ir (µ-Cl)$_2$Ir(abic)$_2$ was synthesized according to the Nonoyama route, by refluxing $IrCl_3.nH_2O$ with 2-2.5 equiv of azabenzoisocoumarin in a 3:1 mixture of 2-ethoxyethanol and water. The chloro-bridged dimer complex (1 g) and silver triflate (0.44 g) were placed in a 100 ml round bottomed flask with 30 ml of acetonitrile and the mixture was degassed, and then refluxed for 4 hours under nitrogen atmosphere. After cooling, the yellow solution was filtered to remove insoluble material and solvent was removed under vacuum. The resulting solid was dried to afford 0.76 g of yellow product. Analysis by mass spectrometry confirmed that this material was bis(acetonitrile)bis[(abic)$_2$]iridium(III) triflate.

Bis(acetonitrile)bis[(abic)$_2$]iridium(III) triflate and 2-phenylpyridine (0.29 ml) were placed in a 100 ml round bottomed flask with 35 ml of 1,2-propanediol and the mixture was degassed, and then refluxed for 12 hours under nitrogen atmosphere during which time an orange precipitate appeared. After cooling, the precipitate was collected by filtration, washed with ethanol and dried to afford 0.5 g of product. Analysis by NMR, mass spectrometry, and high-performance HPLC confirmed that this material was fac-Ir(azabenzoisocoumarin)$_2$(ppy) of high purity. MS: m/z calcd 740. found 741 [M+1]. The photoluminescent quantum yield of the compound in $CH_2Cl_2$ is 40% with maximum emission wavelength at 544 nm.

Synthesis of fac-Ir(azabenzoisocoumarin)$_3$ (INV-20): Cyclometalated Ir(III) µ-chloro-bridged dimer of (abic)$_2$Ir(µ-Cl)$_2$Ir(abic)$_2$ was synthesized according to the Nonoyama route, by refluxing $IrCl_3.nH_2O$ with 2-2.5 equiv of azabenzoisocoumarin in a 3:1 mixture of 2-ethoxyethanol and water. The chloro-bridged dimer complex (0.9 g) and silver triflate (0.40 g) were placed in a 100 ml round bottomed flask with 30 ml of acetonitrile and the mixture was degassed, and then refluxed for 4 hours under nitrogen atmosphere. After cooling, the yellow solution was filtered to remove insoluble material and solvent was removed under vacuum. The resulting solid was dried to afford 0.56 g of yellow product. Analysis by mass spectrometry confirmed that this material was bis(acetonitrile)bis[(abic)$_2$]iridium(III) triflate.

Bis(acetonitrile)bis[(abic)$_2$]iridium(III) triflate and azabenzoisocoumarin (0.36 g) were placed in a 100 ml round bottomed flask with 35 ml of 1,2-propanediol and the mixture was degassed, and then refluxed for 12 hours under nitrogen atmosphere during which time an orange precipitate appeared. After cooling, the precipitate was collected by filtration, washed with ethanol and dried to afford 0.2 g of product. Analysis by NMR, mass spectrometry, and high-performance HPLC confirmed that this material was fac-Ir (azabenzoisocoumarin)$_3$ of high purity. MS: m/z calcd 781; found 782 [M+1]. The photoluminescent quantum yield of the compound in $CH_2Cl_2$ is 42% with maximum emission wavelength at 515 nm.

Examples 10-1 Through 10-6

EL devices (Examples 10-1 through 10-6) satisfying the requirements of the invention were constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon ($CF_x$) hole injecting layer (HIL) was deposited by plasma-assisted deposition of $CHF_3$ as described in U.S. Pat. No. 6,208,075.
3. Next, a hole transporting layer (HTL) of N,N'-di-1-naphthyl-N,N'-diphenyl-4,4'-diaminobiphenyl (NPB)

was vacuum deposited to a thickness of 75 nm for Examples 10-1 through 10-4 and 95 nm for Examples 10-5 and 10-6.
4. A 40 nm light emitting layer (LEL) consisting of a mixture of CBP, and INV-21 as a phosphorescent emitter was then vacuum deposited onto the hole transporting layer. The weight % of the phosphorescent emitter is shown in Table 10.
5. A hole blocking layer of BAlq having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 10-1 had the following structure of layers: ITO|CF$_x$ (1 nm)|NPB (75 nm)|CBP+4 wt. % INV-21 (40 nm)|BAlq (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm$^2$ and the results are reported in Table 1 in the form of luminous yield (cd/A), voltage (V), power efficiency (1 m/W), and CIE (Commission Internationale de l'Eclairage) coordinates. The devices were also tested for operational lifetime. They were operated at 20 mA/cm$^2$ at room temperature with an AC Drive at 100 Hz with a −14 V reverse bias. The lifetime to T$_{60}$ is shown in Table 10 as the number of hours the device operated before the light output dropped to 60% of its initial light output.

TABLE 10

Evaluation results for Devices 10-1 through 10-6.

| Device | Phosphorescent emitter Wt. % | Voltage, V | Luminous Yield, cd/A | Power efficiency, lm/W | CIEx; CIEy | Lifetime, T$_{60}$, hours |
|---|---|---|---|---|---|---|
| 10-1 | 4 | 10.3 | 13.8 | 4.21 | 0.3452 0.5996 | 710 |
| 10-2 | 6 | 10.0 | 13.2 | 4.13 | 0.3570 0.5913 | 1050 |
| 10-3 | 8 | 9.75 | 12.3 | 3.97 | 0.3598 0.5881 | 1370 |
| 10-4 | 10 | 9.72 | 11.4 | 3.68 | 0.3617 0.5845 | 1800 |
| 10-5 | 6 | 10.2 | 13.6 | 4.21 | 0.3650 0.5900 | 1060 |
| 10-6 | 8 | 9.89 | 13.1 | 4.17 | 0.3697 0.5864 | 1840 |

Examples 11-1 Through 11-2

EL devices (Example 11-1 and 11-2) satisfying the requirements of the invention were constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon (CF$_x$) hole injecting layer (HIL) was deposited by plasma-assisted deposition of CHF$_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 95 nm.
4. A exciton blocking layer (EBL) of TCTA was vacuum deposited over the HTL to a thickness of 10 nm.
5. A 35 nm light emitting layer (LEL) consisting of a mixture of TPBI, TCTA, and INV-21 as a phosphorescent emitter was then vacuum deposited onto the exciton blocking layer. The layer consisted of 30% TCTA by weight, the amount of the phosphorescent emitter is shown in Table 2, and the remainder of the layer was TPBI.
5. A hole blocking layer of TPBI having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 11-1 had the following structure of layers: ITO|CF$_x$ (1 nm)|NPB (95 nm)|TCTA (10 nm)|TCTA (30%)+TPBI (62%)+INV-21 (8%) (35 nm)|TPBI (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm$^2$ and the results are reported in Table 11 in the form of luminous yield (cd/A), voltage (V), power efficiency (1 m/W), and CIE (Commission Internationale de l'Eclairage) coordinates.

TABLE 11

Evaluation results for Devices 11-1 through 11-2.

| Device | Phosphorescent emitter Wt. % | Voltage, V | Luminous Yield, cd/A | Power efficiency, lm/W | CIEx; CIEy |
|---|---|---|---|---|---|
| 11-1 | 8 | 4.95 | 75 | 47.6 | 0.3881 0.5907 |
| 11-2 | 10 | 4.76 | 74.5 | 49.2 | 0.3914 0.5882 |

Example 12-1

An EL device (Example 12-1) not satisfying the requirements of the invention was constructed in the following manner:

1. A glass substrate, coated with an approximately 25 nm layer of indium-tin oxide (ITO) as the anode, was sequentially ultrasonicated in a commercial detergent, rinsed in deionized water, degreased in toluene vapor and exposed to an oxygen plasma for about 1 minute.
2. Over the ITO a 1 nm fluorocarbon (CF$_x$) hole injecting layer (HIL) was deposited by plasma-assisted deposition of CHF$_3$ as described in U.S. Pat. No. 6,208,075.
3. Next, a hole transporting layer (HTL) of N,N'-di-1-naphthyl-N,N'-diphenyl-4,4'-diaminobiphenyl (NPB) was vacuum deposited to a thickness of 95 nm for Examples 12-1.
4. A 35 nm light emitting layer (LEL) consisting of a mixture of CBP, and 6 weight % of Ir(ppy)$_3$ as a phosphorescent emitter was then vacuum deposited onto the hole transporting layer.

5. A hole blocking layer of BAlq having a thickness of 10 nm was vacuum deposited over the LEL.
6. An electron transporting layer (ETL) of Alq having a thickness of 40 nm was vacuum deposited over the hole blocking layer.
7. 0.5 nm of lithium fluoride was vacuum deposited onto the ETL, followed by a 100 nm layer of aluminum, to form a bilayer cathode.

The above sequence completed the deposition of the EL device. Therefore, Example 12-1 had the following structure of layers: ITO|CF$_x$ (1 nm)|NPB (95 nm)|CBP+6 wt. % Ir(ppy)$_3$ (35 nm)|BAlq (10 nm)|Alq (40 nm)|LiF|Al. The device, together with a desiccant, was then hermetically packaged in a dry glove box for protection against ambient environment.

The cells thus formed were tested for efficiency and color at an operating current density of 1 mA/cm$^2$ and the results are reported in Table 12 in the form of luminous yield (cd/A), voltage (V), power efficiency (1 m/W), and CIE (Commission Internationale de l'Eclairage) coordinates. The devices were also tested for operational lifetime. They were operated at 20 mA/cm$^2$ at room temperature with an AC Drive at 100 Hz with a −14 V reverse bias. The lifetime to $T_{50}$ is shown in Table 3 as the number of hours the device operated before the light output dropped to 50% of its initial light output.

TABLE 12

Evaluation results for Device 12-1.

| Device | Phosphorescent emitter Wt. % | Voltage, V | Luminous Yield, cd/A | Power efficiency, lm/W | CIEx; CIEy | Lifetime, $T_{50}$, hours |
|---|---|---|---|---|---|---|
| 12-1 | 6 | 6.10 | 34.2 | 17.6 | 0.3018 0.6255 | 173 |

The results with Inventive Example 10-2 relative to Comparison Example 12-1 shows that an organometallic coumarin compound is advantaged over a similar material without the coumarin ligand. In particular the lifetime is improved by approximately 6×.

The invention has been described in detail with particular reference to certain preferred embodiments thereof, but it will be understood that variations and modifications can be effected within the spirit and scope of the invention. The patents and other aforementioned publications are incorporated herein by reference.

PARTS LIST

101 Substrate
103 Anode
105 Hole-Injecting layer (HIL)
107 Hole-Transporting layer (HTL)
108 Exciton Blocking Layer (EBL)
109 Light-Emitting layer (LEL)
110 Hole Blocking Layer (HBL)
111 Electron-Transporting layer (ETL)
113 Cathode
150 Current/Voltage source
160 Electrical conductors

What is claimed is:

1. An OLED device comprising a cathode, an anode, and having therebetween a light emitting layer comprising a phosphorescent emitter represented by Formula (V):

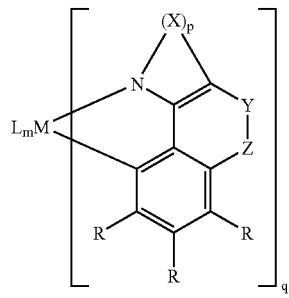

(V)

wherein;
    M is Ir or Pt;
    each L independently represents a cyclometallated ligand;
    each X independently represents the atoms necessary to form a substituted or unsubstituted ring;
    each R independently represents hydrogen or a substituent, provided that two adjacent R groups are able to form a ring;
    Y and Z are each independently an oxygen atom and a carbonyl group such that when one is a carbonyl group the other is an oxygen atom;
    p is an integer from 2 to 4;
    m is a integer from 0 to 2; and
    q is a integer from 1 to 3.

2. An OLED device of claim 1 wherein, M is Ir.

3. An OLED device of claim 1 wherein, the phosphorescent emitter is represented by Formula (VI):

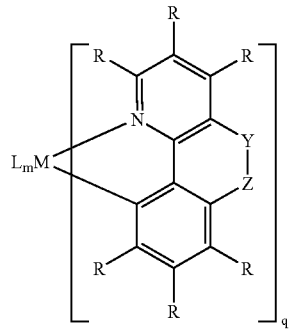

(VI)

wherein;
    each L independently represents a cyclometallated ligand;
    each R independently represents hydrogen or a substituent, provided that two adjacent R groups are able to form a ring;
    Y and Z are each independently an oxygen atom and a carbonyl group such that when one is a carbonyl group the other is an oxygen atom;
    m is a integer from 0 to 2;
    q is a integer from 1 to 3; and
    the sum of m+q is 3.

4. An OLED device of claim 1 wherein, the phosphorescent emitter is represented by Formula (VII):

(VII)

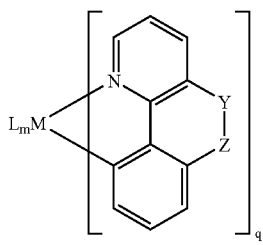

wherein;
each L independently represents a cyclometallated ligand;
Y and Z are each independently an oxygen atom and a carbonyl group such that when one is a carbonyl group the other is an oxygen atom;
m is a integer from 0 to 2;
q is a integer from 1 to 3; and
the sum of m+q is 3.

5. An OLED device of claim 2 wherein the phosphorescent emitter is chosen from the following:

INV-20

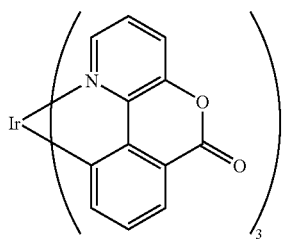

INV-21

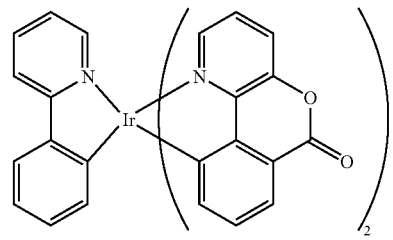

INV-22

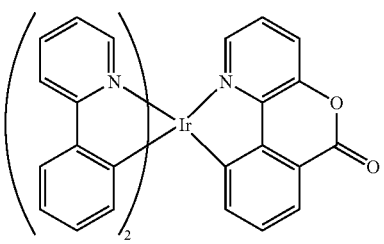 and

INV-23

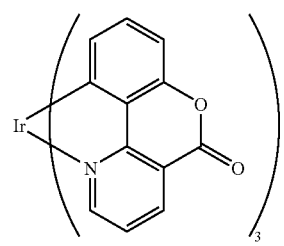.

* * * * *